(12) United States Patent
Dieudonné et al.

(10) Patent No.: US 12,739,573 B2
(45) Date of Patent: Sep. 15, 2026

(54) MAGNIFIED BINAURAL CUES IN A BINAURAL HEARING SYSTEM

(71) Applicant: Cochlear Limited, Macquarie University (AU)

(72) Inventors: Benjamin Dieudonné, Leuven (BE); Tom Francart, Leuven (BE); Zachary Mark Smith, Pymble (AU)

(73) Assignee: Cochlear Limited, Macquarie University (AU)

( * ) Notice: Subject to any disclaimer, the term of this patent is extended or adjusted under 35 U.S.C. 154(b) by 355 days.

(21) Appl. No.: 18/254,038

(22) PCT Filed: Oct. 14, 2021

(86) PCT No.: PCT/IB2021/059456
§ 371 (c)(1),
(2) Date: May 23, 2023

(87) PCT Pub. No.: WO2022/112879
PCT Pub. Date: Jun. 2, 2022

(65) Prior Publication Data

US 2024/0015449 A1 Jan. 11, 2024

Related U.S. Application Data

(60) Provisional application No. 63/119,191, filed on Nov. 30, 2020.

(51) Int. Cl.
*H04R 25/00* (2006.01)
*A61N 1/05* (2006.01)

(52) U.S. Cl.
CPC ......... *H04R 25/407* (2013.01); *H04R 25/405* (2013.01); *H04R 25/507* (2013.01);
(Continued)

(58) Field of Classification Search
CPC ...... H04R 25/407; H04R 1/406; H04R 3/005; H04R 25/405; H04R 25/507;
(Continued)

(56) References Cited

U.S. PATENT DOCUMENTS 8,503,704 B2 8/2013 Francart et al.
9,407,999 B2 8/2016 Brown
(Continued)

FOREIGN PATENT DOCUMENTS

EP 3108929 A1 12/2016
WO 2018038820 A1 3/2018
(Continued)

OTHER PUBLICATIONS

Dieudonné, Benjamin et al: "Head shadow enhancement with fixed beamformers improves sound localized based on interaural level differences", arxiv.org, Cornell University Library, 201 Olin Library Cornell University Ithica, NY 14853, Oct. 5, 2017, XP080826283.
(Continued)

*Primary Examiner* — Norman Yu
(74) *Attorney, Agent, or Firm* — Edell, Shapiro & Finnan, LLC

(57) ABSTRACT

Binaural hearing systems presented herein are configured to provide a recipient with magnified binaural cues. In certain embodiments, the techniques presented herein use static sideways beamforming with interaural magnification to capture and prepare sound signals for subsequent processing. That is, sound signals are captured at each of the binaural prostheses in accordance with a sideways directional pattern (e.g., directional patterns facing away from the head of the recipient). The sound signals captured with the sideways directional patterns, referred to as sideways directional signals, are then used to perform interaural magnification. In other embodiments, the techniques presented herein use
(Continued)

constrained adaptive beamformers to capture sound signals for subsequent processing. In further embodiments, a hearing device of a binaural hearing system is configured to automatically select between the use of static sideways beamforming with interaural magnification, the use of adaptive beamformers, and/or other types of microphone directionality.

30 Claims, 19 Drawing Sheets

(52) U.S. Cl.
CPC .......... *H04R 25/552* (2013.01); *A61N 1/0541* (2013.01); *H04R 2225/41* (2013.01); *H04R 2225/67* (2013.01)

(58) Field of Classification Search
CPC .............. H04R 25/552; H04R 2225/41; H04R 2225/67; H04R 2460/13; H04S 2420/01; A61N 1/0541
USPC .................................. 381/23.1, 313, 312, 92
See application file for complete search history.

(56) References Cited

U.S. PATENT DOCUMENTS

| | | | | |
|---|---|---|---|---|
| 10,469,962 | B2 | 11/2019 | Chen et al. | |
| 2006/0115103 | A1 | 6/2006 | Feng et al. | |
| 2012/0093329 | A1 | 4/2012 | Francart et al. | |
| 2015/0201287 | A1* | 7/2015 | Jespersgaard .......... | H04R 25/50 381/321 |
| 2016/0066104 | A1* | 3/2016 | Minnaar ................ | H04R 25/50 381/23.1 |
| 2016/0366522 | A1* | 12/2016 | Hillbratt .............. | H04R 25/606 |
| 2018/0091907 | A1 | 3/2018 | Long et al. | |
| 2018/0103327 | A1* | 4/2018 | Mosgaard ............ | H04R 25/554 |
| 2018/0176702 | A1 | 6/2018 | Boyle et al. | |
| 2019/0246220 | A1* | 8/2019 | Chen .................... | H04R 25/407 |

FOREIGN PATENT DOCUMENTS

| | | | |
|---|---|---|---|
| WO | 2018038821 | A1 | 3/2018 |
| WO | 2018149507 | A1 | 8/2018 |

OTHER PUBLICATIONS

Extended European Search Report in counterpart European Application No. 21897269.3, mailed Sep. 18, 2024, 9 pages.

International Search Report and Written Opinion in counterpart International Application No. PCT/IB2021/059456, mailed Jan. 14, 2022, 8 pages.

Francart et al., "Amplification of interaural level differences improves sound localization in acoustic simulations of bimodal hearing," The Journal of the Acoustical Society of America, vol. 126, Issue 6, 3209-3213, Dec. 14, 2009. https://doi.org/10.1121/1.3243304.

Francart et al., "Enhancement of interaural level differences improves sound localization in bimodal hearing," The Journal of the Acoustical Society of America, vol. 130, Issue 5, 2817-2826, Nov. 16, 2011. https://doi.org/10.1121/1.3641414.

Christopher A. Brown, "Binaural Enhancement for Bilateral Cochlear Implant Users," Ear and Hearing 35(5):p. 580-584, Sep./Oct. 2014. http://doi.org/10.1097/AUD.0000000000000044.

Dieudonné and Francart, "Head shadow enhancement with low-frequency beamforming improves sound localization and speech perception for simulated bimodal listeners," Hearing Research, vol. 363, pp. 78-84, Jun. 2018. https://doi.org/10.1016/j.heares.2018.03.007.

I. L. D. M. Merks, M. M. Boone and A. J. Berkhout, "Design of a broadside array for a binaural hearing aid," Proceedings of 1997 Workshop on Applications of Signal Processing to Audio and Acoustics, New Paltz, NY, USA, 1997, pp. 4 pp. -, doi: 10.1109/ASPAA.1997.625584.

Todd R. Jennings and Gerald Kidd, Jr., "A visually guided beamformer to aid listening in complex acoustic environments," Proceedings of Meetings on Acoustics, vol. 33, Issue 1, May 7, 2018. https://doi.org/10.1121/2.0000972.

David Yun, Todd R. Jennings, Christine Mason, Gerald Kidd, and Matthew Goupell, "Benefits from different types of acoustic beamforming in bilateral cochlear-implant listeners," The Journal of the Acoustical Society of America, vol. 145, Issue 3, 1876-1877, Mar. 1, 2019. https://doi.org/10.1121/1.5101790.

N. I. Durlach and X. D. Pang, "Interaural magnification," The Journal of the Acoustical Society of America, vol. 80, Issue 6, 1849-1850, Dec. 1, 1986. https://doi.org/10.1121/1.394252.

B. Kollmeier and J. Peissig, "Speech Intelligibility Enhancement by Interaural Magnification," Acta Oto-Laryngologica, vol. 109, Issue sup469, pp. 215-223, 1990. https://doi.org/10.1080/00016489.1990.12088432.

Birger Kollmeier et al., "Toward a scalable, binaural hearing device: Acoustics, interaural processing, and scene decomposition," The Journal of the Acoustical Society of America, vol. 135, Issue 4, p. 2427, Apr. 1, 2014. https://doi.org/10.1121/1.4878072.

Tobias de Taillez et al., "Acoustic and perceptual effects of magnifying interaural difference cues in a simulated "binaural" hearing aid," International Journal of Audiology, vol. 57, Issue sup3, pp. S81-S91, 2018. https://doi.org/10.1080/14992027.2017.1308564.

* cited by examiner

COCHLEAR IMPLANT 102R
EXTERNAL COMPONENT 104R
115
SKIN/TISSUE
SOUND PROCESSING UNIT 106R
113R
118R
122R
108R
MICROPHONE(S)
RF TRANSCEIVER
AUXILIARY INPUT DEVICE(S)
POWER SOURCE
123R
119R
WIRELESS TRANSCEIVER
120R
124R
PROCESSOR(S)
125R
128R
126R
MEMORY
SOUND PROCESSING LOGIC
127R
IMPLANTABLE COIL 114R
138R
134R
146R
140R
142R
RF INTERFACE CIRCUITRY
N
STIMULATOR UNIT
144R
116R
136R
112R IMPLANTABLE COMPONENT

Figure 7:
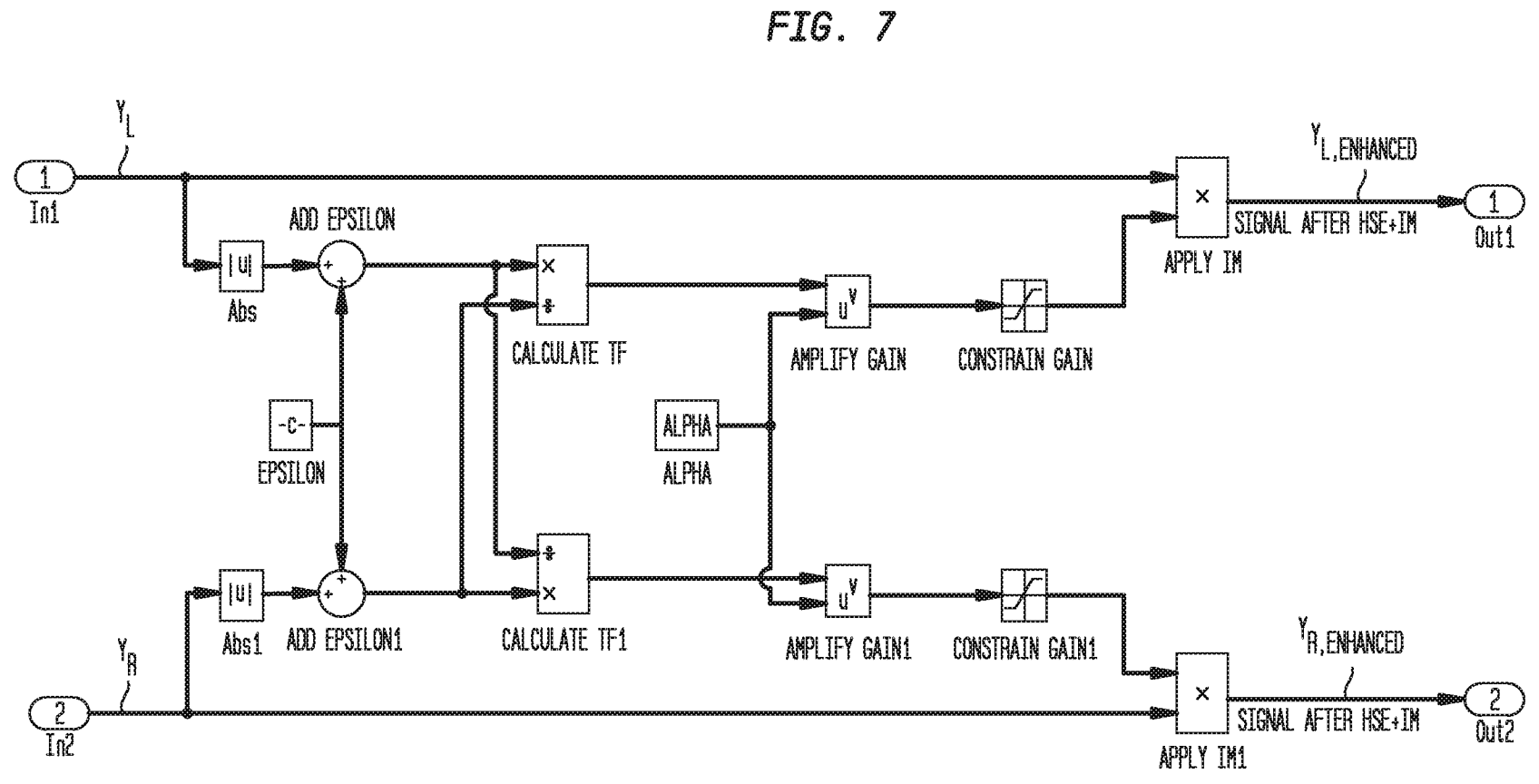

In1
$Y_L$
Abs
ADD EPSILON
EPSILON
-C-
CALCULATE TF
ALPHA
AMPLIFY GAIN
CONSTRAIN GAIN
APPLY IM
SIGNAL AFTER HSE+IM
$Y_{L,ENHANCED}$
Out1
In2
$Y_R$
Abs1
ADD EPSILON1
CALCULATE TF1
AMPLIFY GAIN1
CONSTRAIN GAIN1
APPLY IM1
SIGNAL AFTER HSE+IM
$Y_{R,ENHANCED}$
Out2

862(L)
862(R)
U Y
HIGHPASS_LEFT
LOWPASS_LEFT
LOWPASS_RIGHT
HIGHPASS_RIGHT
In1 Out1
In2 Out2
HSE
870
1
HIGHPASS_LEFT1
LOWPASS_LEFT1
LOWPASS_RIGHT1
HIGHPASS_RIGHT1
IM
872
874(L)
Y L,ENHANCED
Y R,ENHANCED
874(R)

20-250 Hz 250-500 Hz 500-1000 Hz 1000-2000 Hz 2000-4000 Hz
ILD(dB)
20
15
10
5
0
-5
-10
-15
-20
-50
0
50
ANGLE OF INCIDENCE (DEGREES)
NO HSE, ALPHA=0 (NO IM)
HSE90, ALPHA=0 (NO IM)
HSE60, ALPHA=0 (NO IM)
HSE90, ALPHA=2 (IM)
HSE60, ALPHA=2 (IM)

FIG. 10

MIC 1
MIC 2
MIC 3
MIC N
FILTER 1
FILTER 2
FILTER 3
FILTER N
STIMULATION

| DIRECTIONALITY CATEGORY | MICROPHONE DIRECTIONALITY | SNR/ICR | RECIPIENT NEED |
|---|---|---|---|
| QUIET, AND SPEECH-IN-QUIET | STATIC SIDEWAYS BEAMFORMING WITH INTERAURAL MAGNIFICATION | HIGH (e.g.>+10dB) | ACCURATE SOUND LOCALIZATION |
| SPEECH-IN-NOISE OR MULTIPLE TALKERS | ADAPTIVE SIDEWAYS BEAMFORMING | MEDIUM (e.g.>+5dB AND <+10dB) | SOME COMPETING SOUND ATTENUATION BY INCREASING ISOLATION OF IPSILATERAL SOUNDS |
| NOISE | FORWARD-FACING MICROPHONE DIRECTIONALITY | LOW (e.g.<+5dB) | MAXIMUM ATTENUATION OF SOUNDS NOT FROM THE FRONT |

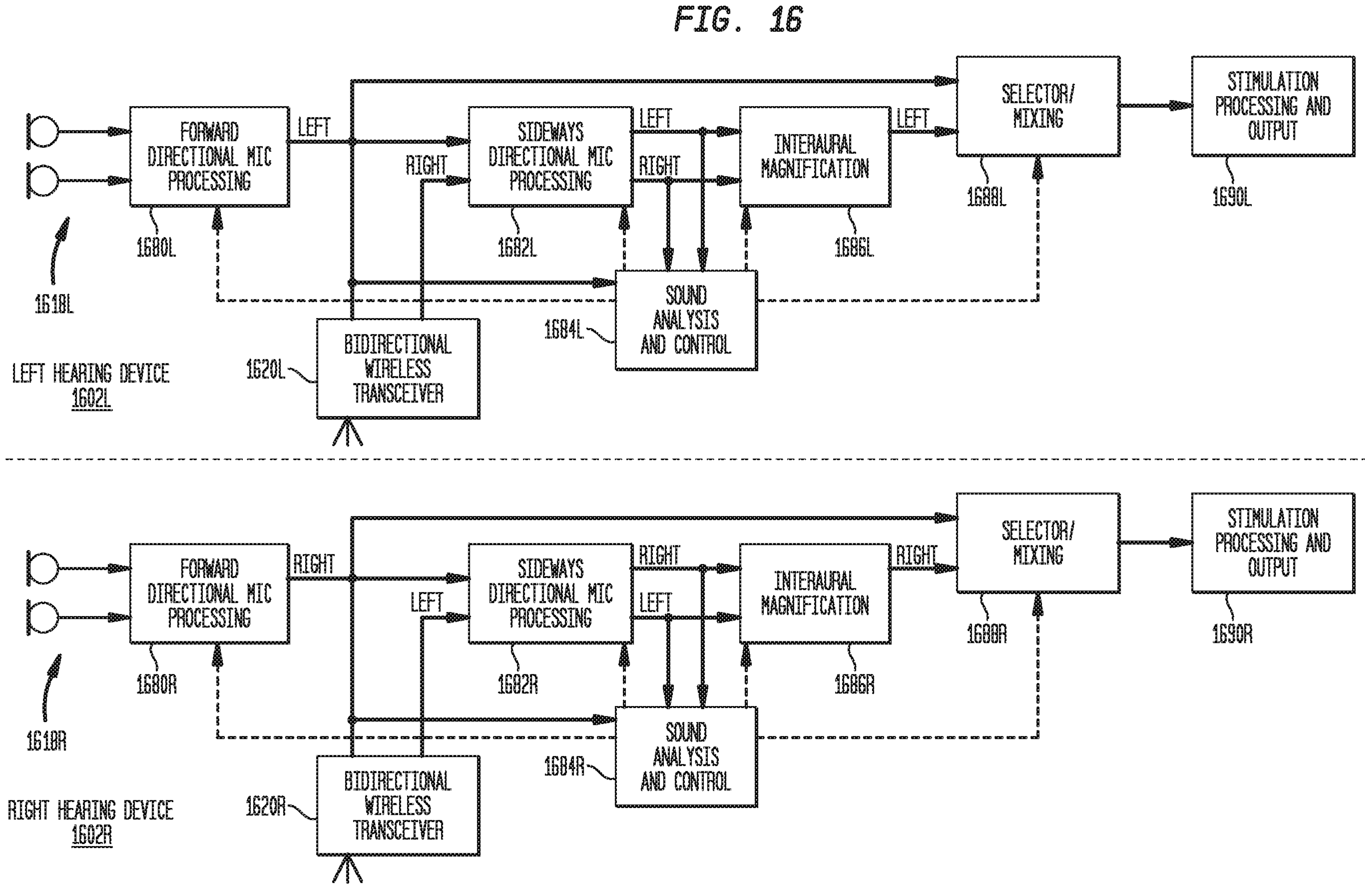
FIG. 16
FORWARD DIRECTIONAL MIC PROCESSING
LEFT
SIDEWAYS DIRECTIONAL MIC PROCESSING
RIGHT
LEFT
RIGHT
INTERAURAL MAGNIFICATION
LEFT
SELECTOR/ MIXING
STIMULATION PROCESSING AND OUTPUT
1680L
1682L
1686L
1688L
1690L
1618L
SOUND ANALYSIS AND CONTROL
1684L
LEFT HEARING DEVICE 1602L
1620L
BIDIRECTIONAL WIRELESS TRANSCEIVER
FORWARD DIRECTIONAL MIC PROCESSING
RIGHT
SIDEWAYS DIRECTIONAL MIC PROCESSING
LEFT
RIGHT
LEFT
INTERAURAL MAGNIFICATION
RIGHT
SELECTOR/ MIXING
STIMULATION PROCESSING AND OUTPUT
1680R
1682R
1686R
1688R
1690R
1618R
SOUND ANALYSIS AND CONTROL
1684R
RIGHT HEARING DEVICE 1602R
1620R
BIDIRECTIONAL WIRELESS TRANSCEIVER

MAGNIFIED BINAURAL CUES IN A BINAURAL HEARING SYSTEM

BACKGROUND

Field of the Invention

The present invention relates generally to binaural hearing systems.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect presented herein, a method is provided. The method comprises: generating a first directional signal from sound signals received at a binaural hearing system comprising a first hearing device positioned at a first ear of a recipient and a second hearing device positioned at a second ear of the recipient, wherein the first directional signal is associated with a first sideways directional pattern; obtaining a second directional signal generated from the sound signals received at the binaural hearing system, wherein the second directional signal is associated with a second sideways directional pattern; performing interaural magnification of the first directional signal relative to the second directional signal to generate a first magnified binaural signal; and generating, based on the first magnified binaural signal, stimulation signals for delivery to the first ear of the recipient via the first hearing device.

In another aspect, a method is provided. The method comprises: capturing sound signals with a first hearing device positioned at a first side of a head of a recipient and a second hearing device positioned at a second side of the head of the recipient; combining, at the first hearing device, the sound signals in a time-dependent manner to generate an output signal in which an output power of sound signals originating from the second side of the head of the recipient is minimized while output power of sound signals coming from the first side of the head of the recipient is preserved; and performing sound processing of the first signal at the first hearing device.

In another aspect, a method is provided. The method comprises: receiving sound signals at a binaural hearing system comprising first and second hearing devices positioned at first and second sides, respectively, of a head of a recipient; at the first hearing device: executing a default interaural magnification microphone directionality mode to pre-process the sound signals, wherein the default interaural magnification microphone directionality mode generates a magnified binaural signal from the sound signals; classifying a sound environment of the first hearing device based on the sound signals; determining a second microphone directionality mode for pre-processing the sound signals based on the classifying of the sound environment; and overriding the default interaural magnification microphone directionality mode with the second microphone directionality mode to generate a second directional signal; and performing sound processing based on the second directional signal.

In another aspect, one or more non-transitory computer readable storage media are provided. The one or more non-transitory computer readable storage media comprise instructions that, when executed by a processor, cause the processor to: perform sideways-facing beamforming of sound signals received at a binaural hearing system, wherein the sideways-facing beamforming generates first and second signals; perform interaural magnification of the first and second signals to generate a magnified binaural signal; and perform sound processing based on the magnified binaural signal.

BRIEF DESCRIPTION OF THE DRAWINGS

Embodiments of the present invention are described herein in conjunction with the accompanying drawings, in which:

FIG. 7 is a schematic diagram generally illustrating interaural magnification, in accordance with certain embodiments presented herein.

FIGS. 10, 11, and 12 are schematic diagram illustrating adaptive constrained beamforming, in accordance with certain embodiments presented herein;

FIG. 13 is a table illustrating example directionality categories and the microphone directionality that would be selected in that directionality categories, in accordance with certain embodiments presented herein;

FIG. 16 is a functional block diagram of an example binaural hearing system, in accordance with certain embodiments presented herein.

DETAILED DESCRIPTION

Figure 1A:
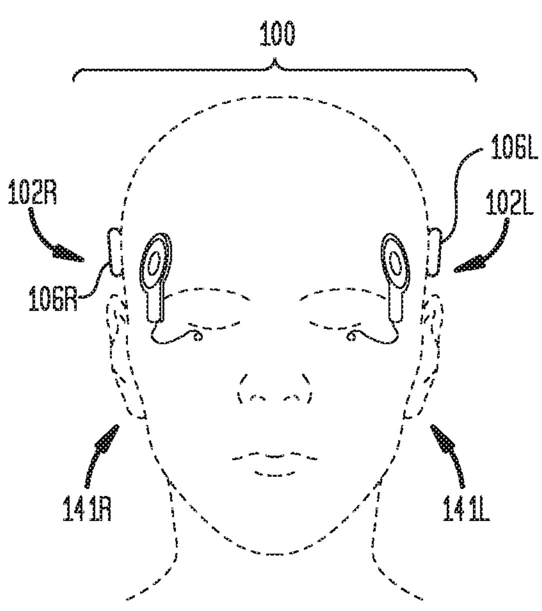
FIG. 1A is a schematic view of a cochlear implant system in which embodiments presented herein may be implemented.

A hearing device system is a type of medical device system that includes one or more hearing devices (e.g., hearing aids, cochlear implants, bone conduction devices, head-worn or external microphones, etc.), that operate to convert sound signals into one or more of acoustic stimulation signals, mechanical stimulation signals, and/or electrical stimulation signals for delivery to a recipient. The one or more hearing devices that can form part of a hearing device system include, for example, hearing aids, cochlear implants, middle ear stimulators, direct acoustic cochlear stimulators, bone conduction devices, brain stem implants, electro-acoustic cochlear implants or electro-acoustic devices, and other devices providing acoustic, mechanical, and/or electrical stimulation to a recipient.

One specific type of hearing device system, referred to herein as a "binaural hearing system" or more simply as a "binaural system," includes two hearing devices positioned at opposing sides (e.g., each ear of the recipient). More specifically, in a binaural system presented herein, each of the two hearing devices includes at least one microphone configured to capture sound signals at a side of the head of the recipient. The hearing devices can comprise any combination of hearing aids, cochlear implants, bone conduction devices, head-worn or external microphones, or other types of devices configured to capture sound signals and/or deliver stimulation of an ear of the recipient. In certain embodiments, a binaural system includes two hearing devices that are each configured to deliver stimulation signals (stimulation) to one of the two ears of the recipient (i.e., either the right or the left ear of the recipient).

Presented herein are binaural hearing device systems (binaural hearing systems) that are configured to provide a recipient with magnified binaural cues. In certain embodiments, the techniques presented herein use static sideways beamforming with interaural magnification to capture and prepare sound signals for subsequent processing. That is, sound signals are captured at each of the binaural prostheses in accordance with a sideways directional pattern (e.g., directional patterns generally facing away from a side of the head of the recipient). The sound signals captured with the sideways directional patterns, referred to as sideways directional signals, are then used to perform interaural magnification. In other embodiments, the techniques presented herein use constrained adaptive beamformers to capture sound signals for subsequent processing. In further embodiments, a hearing device of a binaural hearing system is configured to automatically select between the use of static sideways beamforming with interaural magnification, the use of adaptive beamformers, and/or other types of microphone directionality.

It is to be appreciated that the techniques presented herein may implemented with any of a number of hearing devices or other medical devices, including in conjunction with cochlear implants or other hearing devices, balance prostheses (e.g., vestibular implants), retinal or other visual prostheses, cardiac devices (e.g., implantable pacemakers, defibrillators, etc.), seizure devices, sleep apnea devices, electroporation devices, spinal cord stimulators, deep brain stimulators, motor cortex stimulators, sacral nerve stimulators, pudendal nerve stimulators, vagus/vagal nerve stimulators, trigeminal nerve stimulators, diaphragm (phrenic) pacers, pain relief stimulators, other neural, neuromuscular, or functional stimulators, etc.

However, merely for ease of description, aspects of the techniques will be generally described with reference to a specific medical device system, namely a bilateral cochlear implant system. As used herein, a "bilateral" cochlear implant system is a system that includes first and second cochlear implants located at first and second ears, respectively, of a recipient. In such systems, each of the two cochlear implant system delivers stimulation (current) pulses to one of the two ears of the recipient (i.e., either the right or the left ear of the recipient). In a bilateral cochlear implant system, one or more of the two cochlear implants may also deliver acoustic stimulation to the ears of the recipient (e.g., an electro-acoustic cochlear implant) and/or the two cochlear implants need not be identical with respect to, for example, the number of electrodes used to electrically stimulate the cochlea, the type of stimulation delivered, etc. As noted elsewhere herein, the techniques presented herein may be implemented in other systems, such as binaural hearing systems comprising a hearing aid at a first ear of a recipient and a cochlear implant at a second ear of the recipient.

Figure 1B:
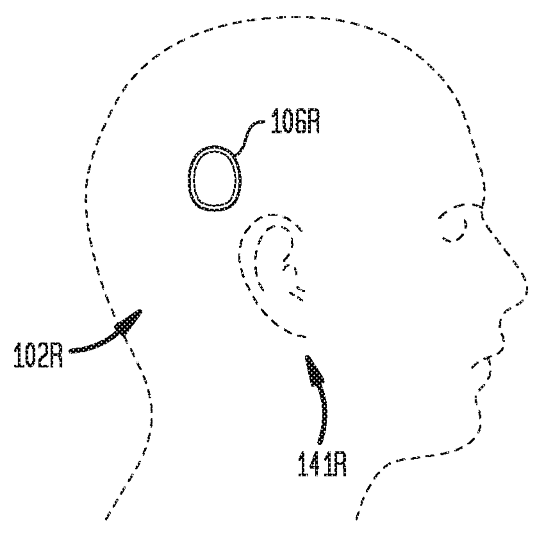
FIG. 1B is a side view of a recipient wearing the cochlear implant system of FIG. 1A.
Figure 1C:
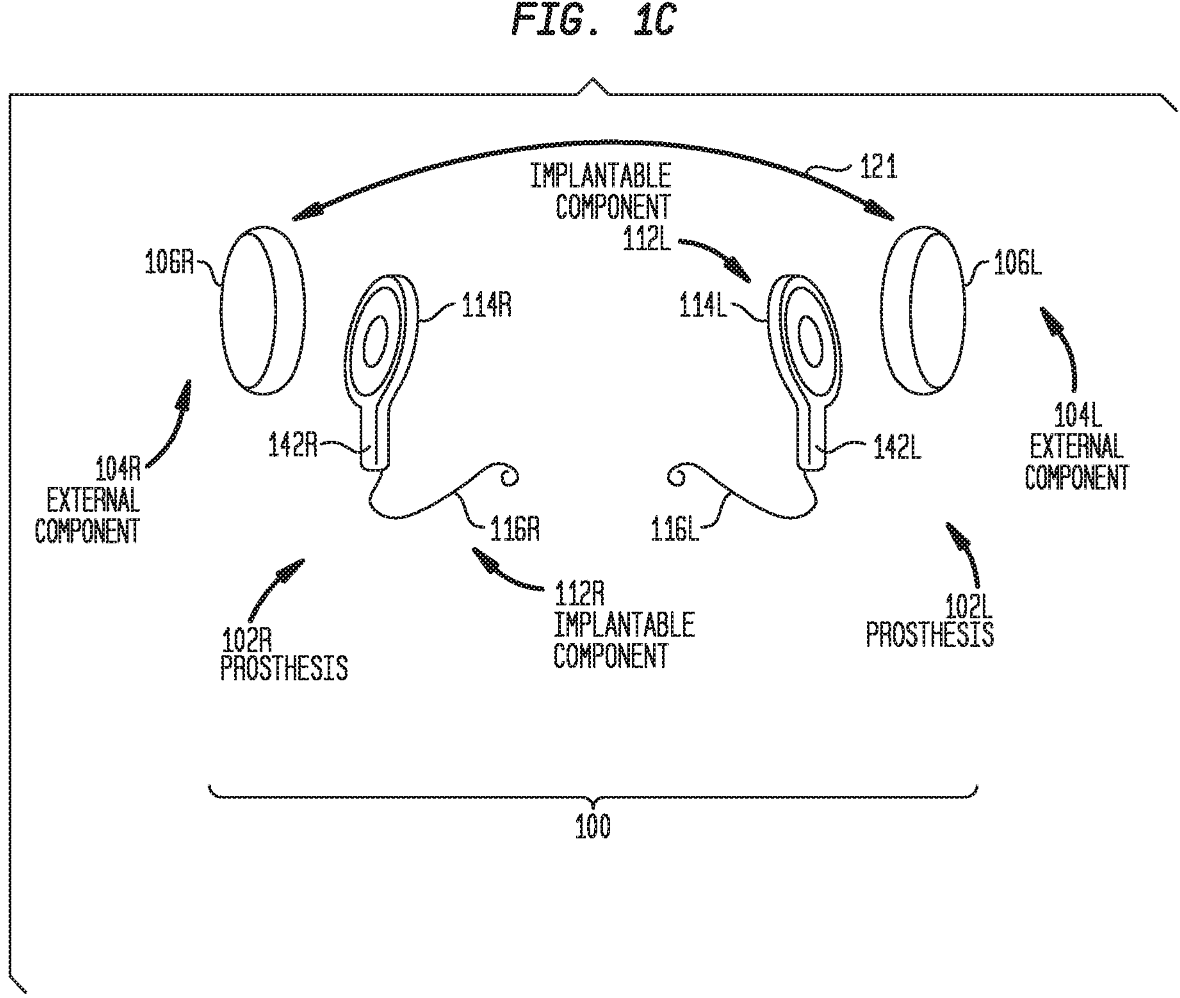
FIG. 1C is a schematic view of the components of the cochlear implant system of FIG. 1A.
Figure 1D:
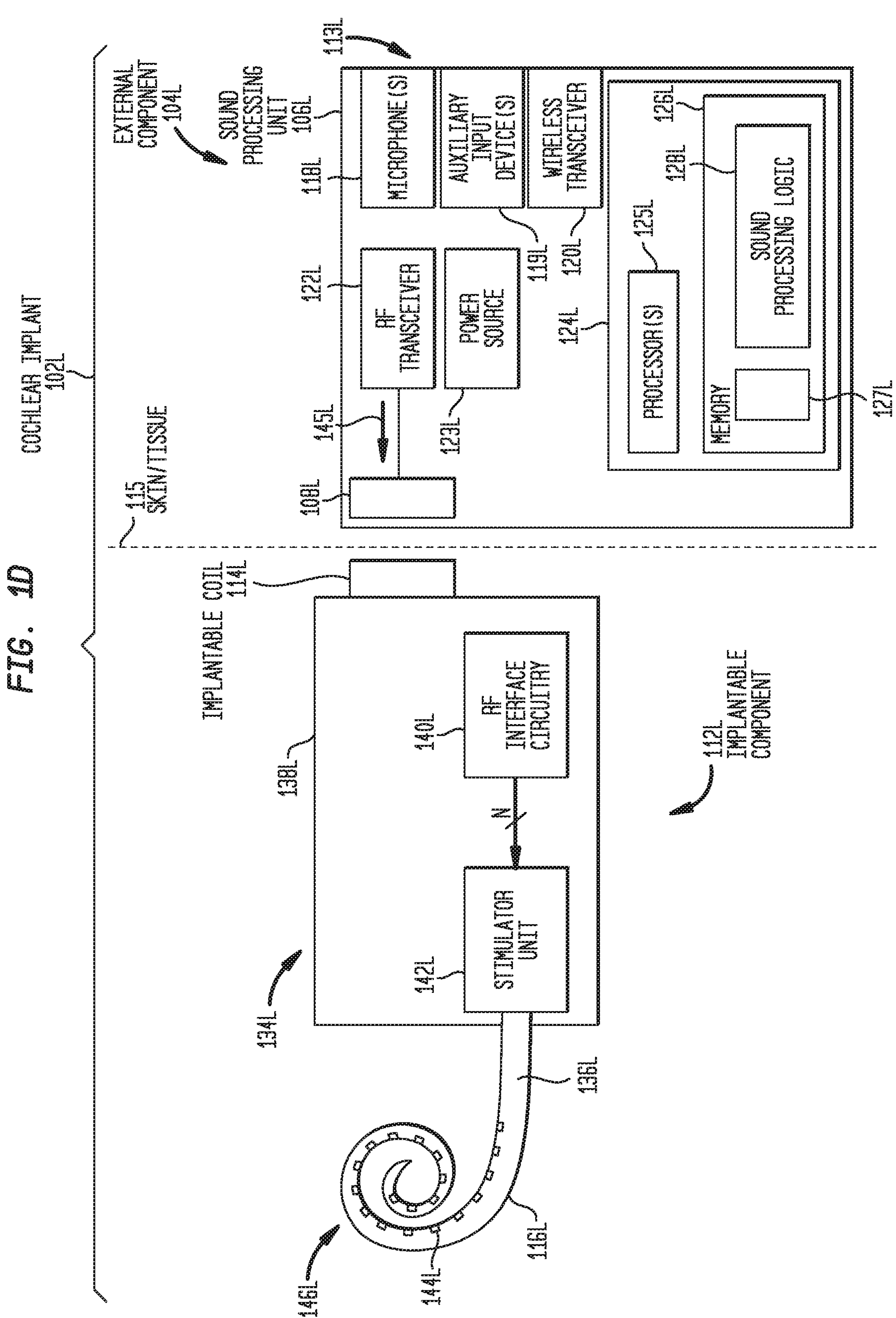
FIGS. 1D and 1E are block diagrams of sound processing units forming part of the cochlear implant system of FIG. 1A.
Figure 1E:
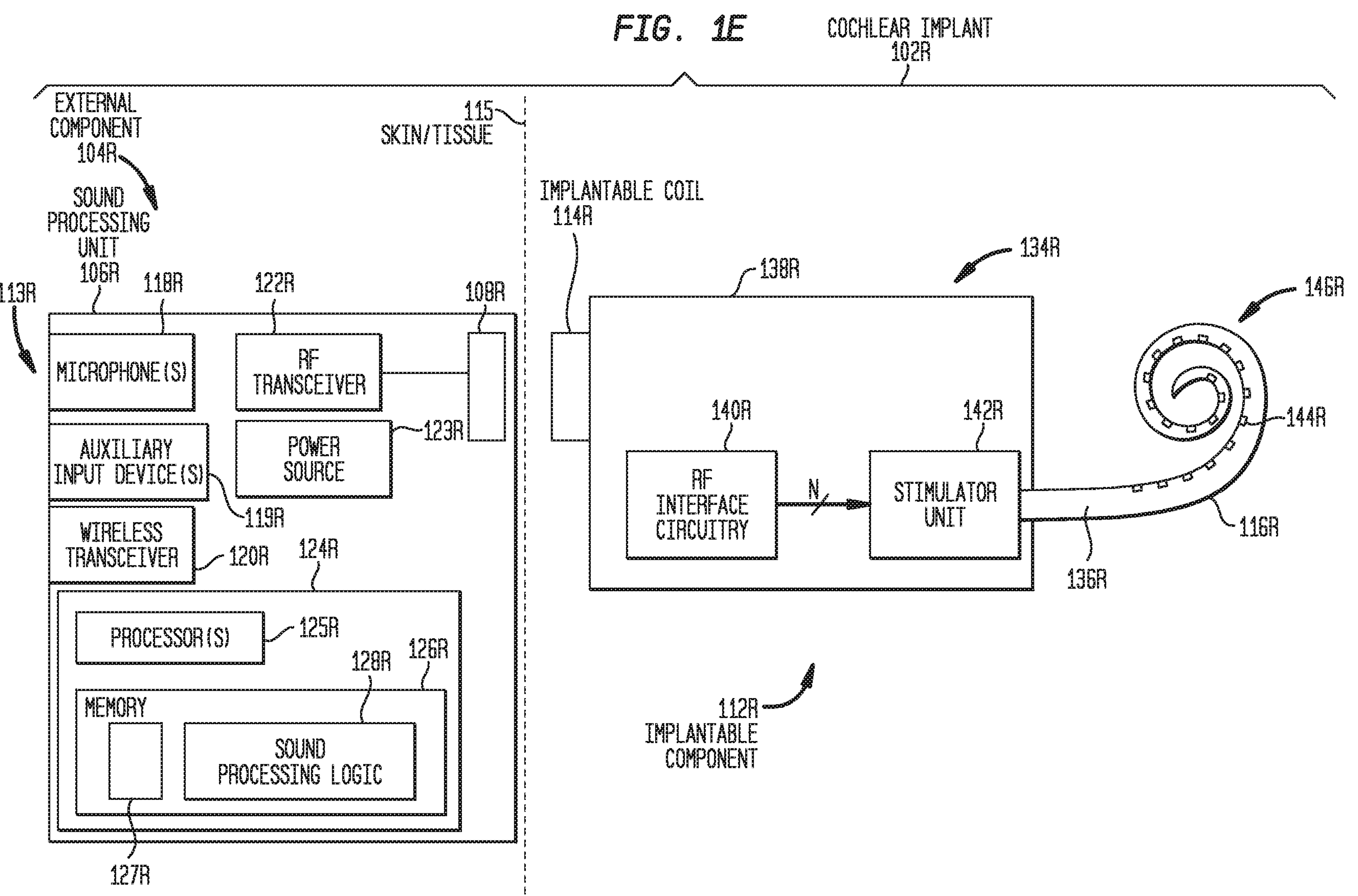

FIGS. 1A-1E are diagrams illustrating one example bilateral cochlear implant system 100 configured to implement the techniques presented herein. More specifically, FIGS. 1A-1E illustrate an example bilateral system 100 comprising left and right cochlear implants, referred to as cochlear implant 102L and cochlear implant 102R. FIGS. 1A and 1B are schematic drawings of a recipient wearing the left cochlear implant 102L at a left ear 141L and the right cochlear implant 102R at a right ear 141R, while FIG. 1C is a schematic view of each of the left and right cochlear implants. FIGS. 1D and 1E are block diagrams illustrating further details of the left cochlear implant 102L and the right cochlear implant 102R, respectively.

Referring specifically to FIG. 1C, cochlear implant 102L includes an external component 104L that is configured to be directly or indirectly attached to the body of the recipient and an implantable component 112L configured to be implanted in the recipient. The external component 104L comprises a sound processing unit 106L, while the implantable component 112L includes an internal coil 114L, a stimulator unit 142L and an elongate stimulating assembly (electrode array) 116L implanted in the recipient's left cochlea (not shown in FIG. 1C). As described further below, the sound processing units 106L and 106R are configured to wirelessly communicate with one another via a bi-directional wireless link 121.

The cochlear implant 102R is substantially similar to cochlear implant 102L. In particular, cochlear implant 102R includes an external component 104R comprising a sound processing unit 106R, and an implantable component 112R comprising internal coil 114R, stimulator unit 142R, and elongate stimulating assembly 116R.

FIG. 1D is a block diagram illustrating further details of cochlear implant 102L, while FIG. 1E is a block diagram illustrating further details of cochlear implant 102R. As noted, cochlear implant 102R is substantially similar to cochlear implant 102L and includes like elements as that described below with reference to cochlear implant 102L. For ease of description, further details of cochlear implant 102R have been omitted from the description.

As noted, the external component 104L of cochlear implant 102L includes a sound processing unit 1061. The sound processing unit 106L comprises one or more input devices 113L that are configured to receive input signals (e.g., sound or data signals). In the example of FIG. 1D, the one or more input devices 113L include one or more microphones 118L and one or more auxiliary input devices 119L (e.g., telecoils, audio ports, such as a Direct Audio Input (DAI), data ports, such as a Universal Serial Bus (USB) port, cable port, etc.), and a wireless transmitter/receiver (transceiver) 120L (e.g., for use with bi-directional wireless link 121 and/or other wireless links). However, it is to be appreciated that one or more input devices 113L may include additional types of input devices and/or less input devices.

The sound processing unit 106L also comprises one type of a closely-coupled transmitter/receiver (transceiver) 122L, referred to as or radio-frequency (RF) transceiver 122L, a power source 123L, and a processing module 124L. The processing module 124L comprises one or more processors 125L and a memory 126L that includes magnified binaural cue logic 127L and sound processing logic 128L. It is to be appreciated that the memory 126L may include other logic that, for ease of illustration and description, have been omitted from FIG. 1D.

In the examples of FIGS. 1A-1E, the sound processing unit 106L and the sound processing unit 106R are off-the-ear (OTE) sound processing units (i.e., components having a generally cylindrical shape and which is configured to be magnetically coupled to the recipient's head), etc. However, it is to be appreciated that embodiments of the present invention may be implemented by sound processing units having other arrangements, such as by a behind-the-ear (BTE) sound processing unit configured to be attached to and worn adjacent to the recipient's ear, including a mini or micro-BTE unit, an in-the-canal unit that is configured to be located in the recipient's ear canal, a body-worn sound processing unit, etc.

The implantable component 112L comprises an implant body (main module) 134L, a lead region 136L, and the intra-cochlear stimulating assembly 116L, all configured to be implanted under the skin/tissue (tissue) 115 of the recipient. The implant body 134L generally comprises a hermetically-sealed housing 138L in which RF interface circuitry 140L and a stimulator unit 142L are disposed. The implant body 134L also includes the internal/implantable coil 114L that is generally external to the housing 138L, but which is connected to the transceiver 140L via a hermetic feed-through (not shown in FIG. 1D).

As noted, stimulating assembly 116L is configured to be at least partially implanted in the recipient's cochlea. Stimulating assembly 116L includes a plurality of longitudinally spaced intra-cochlear electrical stimulating contacts (electrodes) 144L that collectively form a contact or electrode array 146L for delivery of electrical stimulation (current) to the recipient's cochlea.

Stimulating assembly 116L extends through an opening in the recipient's cochlea (e.g., cochleostomy, the round window, etc.) and has a proximal end connected to stimulator unit 142L via lead region 136L and a hermetic feedthrough (not shown in FIG. 1D). Lead region 136L includes a plurality of conductors (wires) that electrically couple the electrodes 144L to the stimulator unit 142L.

As noted, the cochlear implant 102L includes the external coil 108L and the implantable coil 114L. The coils 108L and 114L are typically wire antenna coils each comprised of multiple turns of electrically insulated single-strand or multi-strand platinum or gold wire. Generally, a magnet is fixed relative to each of the external coil 108L and the implantable coil 114L. The magnets fixed relative to the external coil 108L and the implantable coil 114L facilitate the operational alignment of the external coil 108L with the implantable coil 114L. This operational alignment of the coils enables the external component 104L to transmit data, as well as possibly power, to the implantable component 112L via a closely-coupled wireless link formed between the external coil 108L with the implantable coil 114L. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1D illustrates only one example arrangement.

As noted above, sound processing unit 106L includes the processing module 124L. The processing module 124L is configured to convert received input signals (received at one or more of the input devices 113L) into output signals 145L for use in stimulating a first ear of a recipient (i.e., the processing module 124L is configured to magnify binaural cues, as described further below, and to perform sound processing on sound signals received at the sound processing unit 106L). Stated differently, the one or more processors 125L are configured to execute magnified binaural cue logic 127L and sound processing logic 128L to convert the received sound signals into output signals 145L that represent electrical stimulation for delivery to the recipient.

In the embodiment of FIG. 1D, the output signals 145L are provided to the RF transceiver 114, which transcutaneously transfers the output signals 145L (e.g., in an encoded manner) to the implantable component 112L via external coil 108L and implantable coil 114L. That is, the output signals 145L are received at the RF interface circuitry 140L via implantable coil 114L and provided to the stimulator unit 142L. The stimulator unit 142L is configured to utilize the output signals 145L to generate electrical stimulation signals (e.g., current signals) for delivery to the recipient's cochlea via one or more stimulating contacts 144L. In this way, cochlear implant 102L electrically stimulates the recipient's auditory nerve cells, bypassing absent or defective hair cells that normally transduce acoustic vibrations into neural activity, in a manner that causes the recipient to perceive one or more components of the received sound signals.

As noted, cochlear implant 102R is substantially similar to cochlear implant 102L and comprises external component 104R and implantable component 112R. External component 104R includes a sound processing unit 106R that comprises external coil 108R, input devices 113R (i.e., one or more sound input devices 118R, one or more auxiliary input devices 119R, and wireless transceiver 120R), closely-coupled transceiver (RF transceiver) 122R, power source 123R, and processing module 124R. The processing module 124R includes one or more processors 125R and a memory 126R that includes magnified binaural cue logic 127R and sound processing logic 128R. The implantable component 112R includes an implant body (main module) 134R, a lead region 136R, and the intra-cochlear stimulating assembly 116R, all configured to be implanted under the skin/tissue (tissue) 115 of the recipient. The implant body 134R generally comprises a hermetically-sealed housing 138R in which RF interface circuitry 140L and a stimulator unit 142R are disposed. The implant body 134R also includes the internal/implantable coil 114R that is generally external to the housing 138R, but which is connected to the RF interface circuitry 140R via a hermetic feedthrough (not shown in FIG. 1E). The stimulating assembly 116R includes a plurality of longitudinally spaced intra-cochlear electrical stimulating contacts (electrodes) 144R that collectively form a contact or electrode array 146R for delivery of electrical stimulation (current) to the recipient's cochlea. Each of the elements of cochlear implant 102R shown in FIG. 1E are similar to like-numbered elements of cochlear implant 102L shown in FIG. 1D.

Sound localization (e.g., determined the location of the source of sound signals) and speech understanding in complex acoustic environments is generally difficult for binaural (e.g., bilateral or bimodal) hearing device recipients (binaural recipients). The acoustic head shadow (head shadow) or head shadow effect is one mechanism that assists binaural recipients with both sound localization and speech understanding. In general, the head shadow or the head shadow effect refers to the fact that each ear of a recipient is in the acoustic shadow of sounds originating from the opposite side of the head. The head shadow helps speech intelligibility when a competing sound is at one side of the head, since it will generally lead to a favorable signal-to-noise ratio (SNR) at the other ear.

Figure 2:
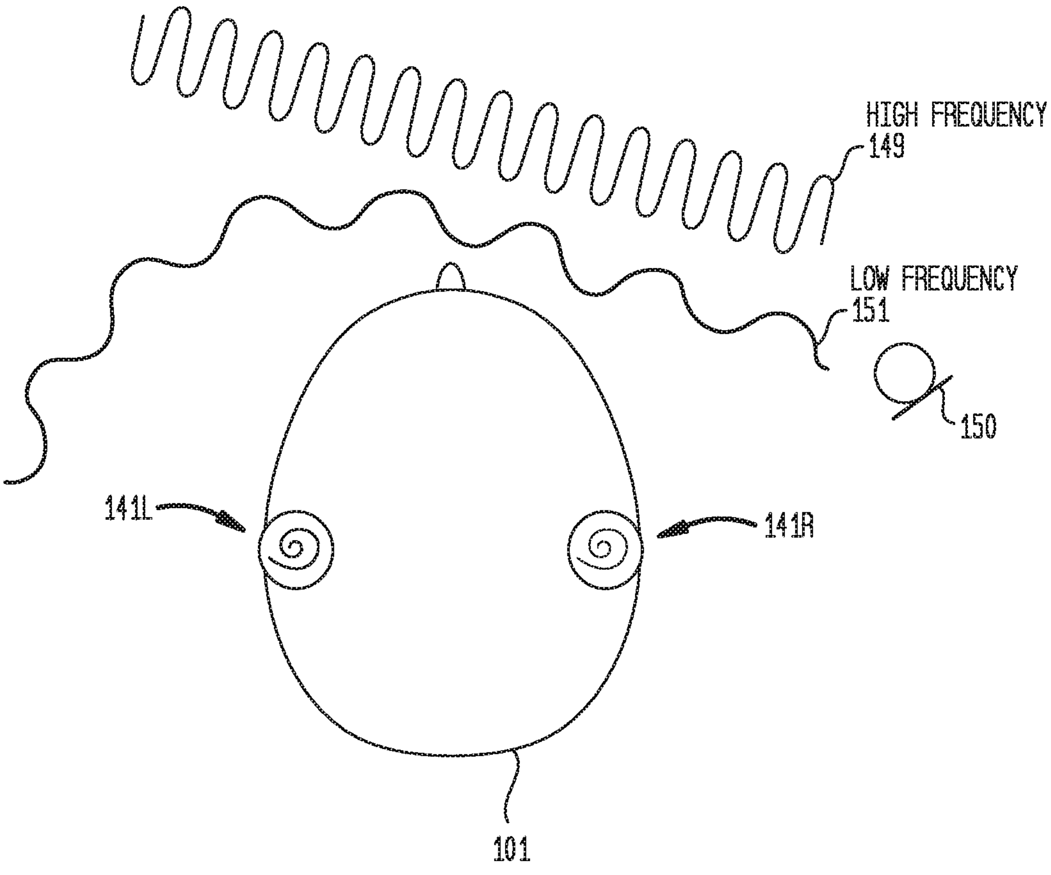
FIG. 2 is a schematic diagram illustrating the head shadow effect for sound signals originating from a right side of a recipient.

FIG. 2 is a schematic diagram that illustrates the head shadow effect at the head 101 of the recipient of cochlear implant system 100 of FIG. 1. As shown, a sound source 150 is located adjacent the right ear 141R of the recipient and, as a result, the sound source 150 is in head shadow of the contralateral left ear 141L.

FIG. 2 illustrates high frequency sound signals (sounds) 149 and low frequency sounds 151 (with wavelengths not drawn to scale) originating from the right side of the head 101 (i.e., the spatial region generally proximate to the ear 141R). The low frequency sounds 151, due to their long wavelength, readily bend around the recipient's head 101 and, as such, are largely unaffected by the presence of the head. However, high frequency sounds 149 have shorter wavelengths and, as such, tend to be reflected by the recipient's head 101. As a result, the higher frequency sounds 149 originating from the right side are not well received at the left ear 141L. When considering that consonant sounds, which contain much of the meaning of English speech, generally occur in the higher-frequency domain, the head shadow effect can be the root cause for the difficulty in communication experienced by individuals suffering from single-sided deafness, especially as it relates to speech understanding in the presence of background noise.

In certain examples, frequencies generally above 1.5 kilohertz (kHz) are reflected and are "shadowed" by the recipient's head, while frequencies below 1.5 kHz will bend around the head. Generally speaking, a reason that frequencies below 1.5 kHz are not affected (i.e., bend around the head) is due to the wavelength of such frequencies being in the same order as the width of a normal recipient's head. Therefore, as used herein, "high frequency sounds" or "high frequency sound signals" generally refer to signals having a frequency approximately greater than about 1.5 kHz, while "low frequency sounds" or "low frequency sound signals" refer to signals having a frequency approximately less than about 1.5 kHz. However, it is to be appreciated that the actual cut-off frequencies may be selected based on a variety of factors, including, but not limited to, the size of a recipient's head.

In practice, the head shadow effect introduces Interaural (Inter-aural) Level Differences (ILDs), which are helpful for sound localization, and which provide a means to identify an acoustically "better-ear" (ear with higher SNR), if speech and noise sources arrive from different directions in the horizontal plane. However, as noted, the head shadow effect is small or non-existent at lower frequencies and, as a result, the ILDs may not be present and/or may be very small in the lower frequency ranges. As such, recipients of conventional binaural prostheses typically do not have access to ILDs in the lower frequency bands/ranges, which negatively affects sound localization, speech understanding, etc.

Accordingly, certain embodiments presented herein are directed to techniques for introducing ILDs within the lower frequency ranges of in sound signals captured by a binaural prostheses through the use of opposing sideways directional signals. Additionally, the techniques presented herein magnify/amplify the ILDs introduced into the lower frequency ranges, potentially with the naturally occurring ILDs in the higher frequency ranges, to make the ILDs more prevalent for subsequent processing. In other words, the techniques presented herein can create a broadband (as opposed to only in the high frequencies) amplified acoustic head shadow through the use of microphones available at the two sides of the head of the recipient.

In certain embodiments, the amplified acoustic head shadow is created through the use of static sideways beamforming with interaural (ILD) magnification. In such embodiments, sideways-facing microphone directionality patterns (e.g., left device pointing more left, right device pointing more right) are used to capture sound signals and interaural magnification is applied, potentially at all frequencies, to further enhance the ILDs.

In certain embodiments presented herein, constrained adaptive beamforming is applied to capture sound signals. Constrained adaptive beamforming refers to adaptively steering beamformer directionality patterns to minimize noise power from the contralateral side (e.g., left device minimizes power from right side, right device minimizes power from left side). The techniques presented herein can provide improved sound localization accuracy for binaural recipients and improve hearing in noise when the target and masking sources arrive from different directions in the horizontal plane, while maintaining spatial awareness.

Figure 11:
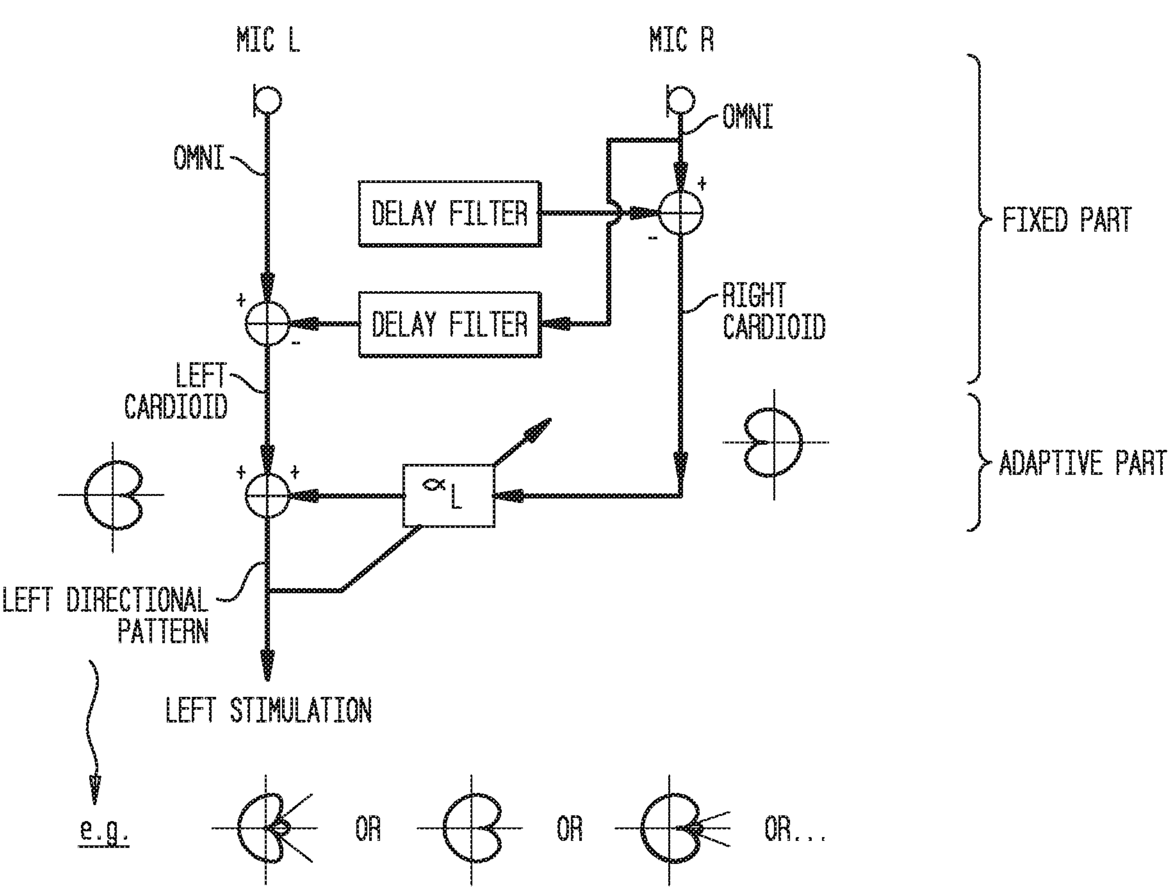

The use of static sideways beamformers with interaural (ILD) magnification is generally described below with reference to FIGS. 3-9. Constrained adaptive beamforming is generally described below with reference to FIGS. 10-12. An example combining the use of static sideways beamformers with interaural (ILD) magnification with constrained adaptive beamformers is described below with reference to FIG. 13.

As noted, certain embodiments presented herein use static sideways-facing beamforming with interaural magnification to create a large and broadband amplification of the head shadow that can be tuned. These techniques enhance binaural cues without the need for explicit estimations of sound sources and their locations. Static sideways-facing beamforming and interaural magnification are each first described separately below, following by a description of the static sideways-facing beamforming with the interaural magnification.

In the context of hearing devices, "beamforming" is an array sound processing technique configured to enhance (capture) sounds from one or more directions, while simultaneously suppressing sounds (e.g., noise and interferences) from other directions. As such, beamforming creates a directional audio pickup pattern having maximum sensitivity to sounds originating from a target/primary direction/angle and decreased sensitivity to sounds originating from directions/angles other than the primary direction. The directional audio pickup pattern is often referred to as a polar pattern and polar patterns are often represented as a plot of sensitivity to sounds at different angles for different frequencies, known as polar plots. A "beamformer" is a system that uses one or more microphone arrays to perform the beamforming, namely to generate a directional sound signal in accordance with a specific directionality pattern.

As used herein, static sideways beamforming refers to the generation of two "sideways-facing" or "lateral-facing" directionality patterns, relative to the head of a recipient. For example, in a binaural hearing system, the left-side hearing device has a directionality pattern pointing more left (minimum sensitivity at the contralateral/right side of the head of the recipient) and the right-side hearing device has a pattern pointing more right (minimum sensitivity facing at the contralateral/left side of the head of the recipient).

As used herein, "directional sound signals" are signals that are generated from sound signals captured at a microphone array in accordance with a specific directionality pattern (e.g., the received sound signals are processed to generate the specific pattern of maximum sensitivity to sounds originating from a target/primary direction/angle and decreased sensitivity to sounds originating from directions/angles other than the primary direction). Also as used herein, "sideways-facing directional signals" are signals that are generated in accordance with sideways-facing directionality patterns.

Figures 3A, 3B:
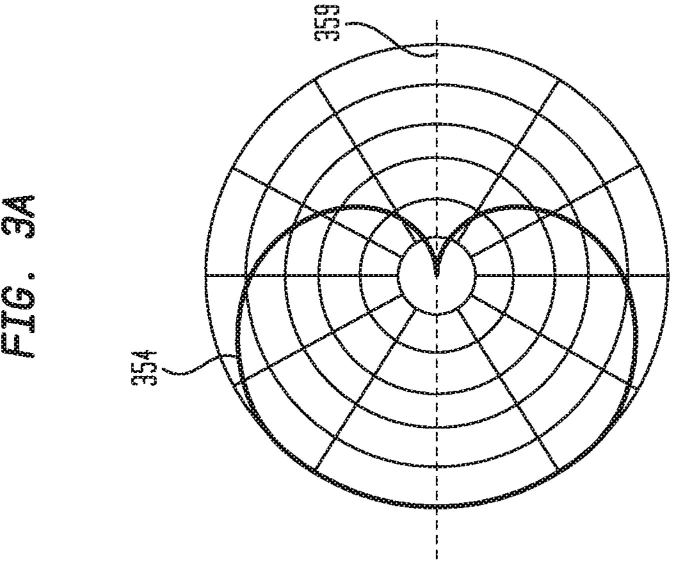
FIG. 3A is a polar plot illustrating a cardioid directional pattern of a static sideways beamformer, in accordance with certain embodiments presented herein.
FIG. 3B is a polar plot illustrating a supercardioid directional pattern of a static sideways beamformer, in accordance with certain embodiments presented herein.

Two example sideways-facing directionality patterns associated with a left-side prosthesis, such as cochlear implant 102L, are shown in FIGS. 3A and 3B. More specifically, FIG. 3A illustrates an example cardioid polar pattern 354 that can be generated by a static sideways beamformer, in accordance with certain embodiments presented herein, while FIG. 3B illustrates an example supercardioid polar pattern 356 that can be generated by a static sideways beamformer, in accordance with other embodiments presented herein. In FIG. 3A, the null is generally located at 90 degrees, while in FIG. 3B the null is located round 60 degrees, with its null directions at the right side. The directionality of the patterns 354 and 365 are fixed/static, but the patterns can be frequency-dependent. That is, in accordance with certain embodiments, the microphone directionality patterns can be different within different frequencies (e.g., supercardioid polar pattern in one frequency band, a cardioid polar pattern in another frequency pattern, etc.).

It is to be appreciated that the two sideways-facing directionality patterns shown in FIGS. 3A and 3B are merely illustrative and that different and/or more complex sideways-facing directionality patterns may be used in alternative embodiments. In general, the more microphones in an array and/or the number of microphone arrays available, the more complex the patterns can be designed.

Figure 4:
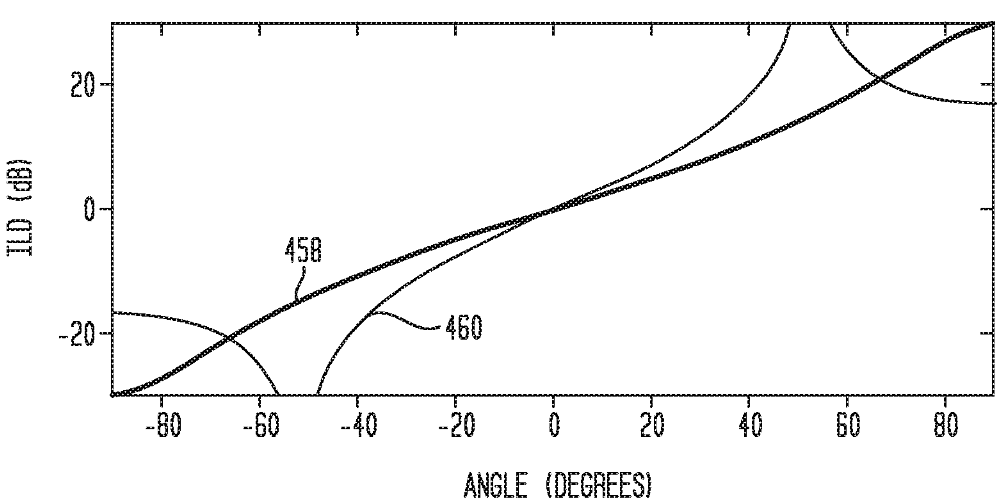
FIG. 4 is a graph generally illustrating two Interaural Difference (ILD) versus angle functions associated with two different directionality patterns, in accordance with certain embodiments presented herein.

Different directionality patterns have different advantages, such as creating different patterns of interaural level differences (ILDs) and different ILD-versus-angle functions. FIG. 4 is a graph generally illustrating two ILD versus angle functions associated with two different directionality patterns. In general, determining ILD as a function of angle involves determining the difference in two polar plots (one for each ear) across angle. For example, if the polar plots are identical, then there would be 0 ILD at all frequencies.

As shown by curve 458, a null at 90 degrees (cardioid polar pattern) creates an ILD pattern that is monotonic between −90 and +90 degrees, which can result in unambiguous localization performance between those angles. However, as shown by curve 460, a null at 60 degrees (supercardioid polar pattern) results in a steeper ILD-vs-angle function, which can result in more precise localization performance at smaller angles. Moreover, the different patterns can also result in different speech understanding benefits, with the supercardioid pattern having more contralateral attenuation in each ear as compared to the cardioid pattern. The different trade-offs of the directionality patterns can be exploited by making the directionality pattern frequency-dependent, e.g., by having a steeper ILD curve in some frequency regions, while preserving monotonic ILD-vs-angle function in another frequency regions. Stated differently, different microphone directionality patterns will create different ILD functions and one could, for example, implement a supercardioid (maximized directionality) in a frequency region that is more important for speech understanding, and, at the same time, a regular cardioid in other frequency regions, to make unambiguous localization between −90 and +90 degrees possible.

Sideways-facing directionality patterns, in accordance with embodiments presented herein, can be generated in a number of different manners. For example, in certain embodiments, sideways-facing directionality patterns can be achieved with a filter-and-sum beamformer. In its simplest form, the filter-and-sum beamformer includes two or more omnidirectional microphones that are positioned along the symmetry axis of the directional pattern in this case, from left to right (e.g., axis 359 in FIGS. 3A and 3B). The more microphones in such a microphone array, the stronger the directional pattern, and the more design flexibility.

In a binaural hearing system, a microphone array can be formed by: (1) adding one (or more) extra microphone(s) on the behind-the-ear (BTE) device in the lateral direction; (2) using a microphone array from an extra device, e.g., a headband, microphones on the shoulders, etc.; or (3) using one or more microphones from the left-side hearing device, and one or more microphones from the right-side hearing device. In general, the third option (e.g., microphones from each of the left-side and right-side prostheses) may be the most practical in many systems as this option does not utilize additional/separate devices or hardware changes. As such, examples provided below are generally described with reference to the use of a filter-and-sum beamformer formed using one or more microphones from a left-side hearing device, and one or more microphones from a right-side hearing device.

Figure 5:
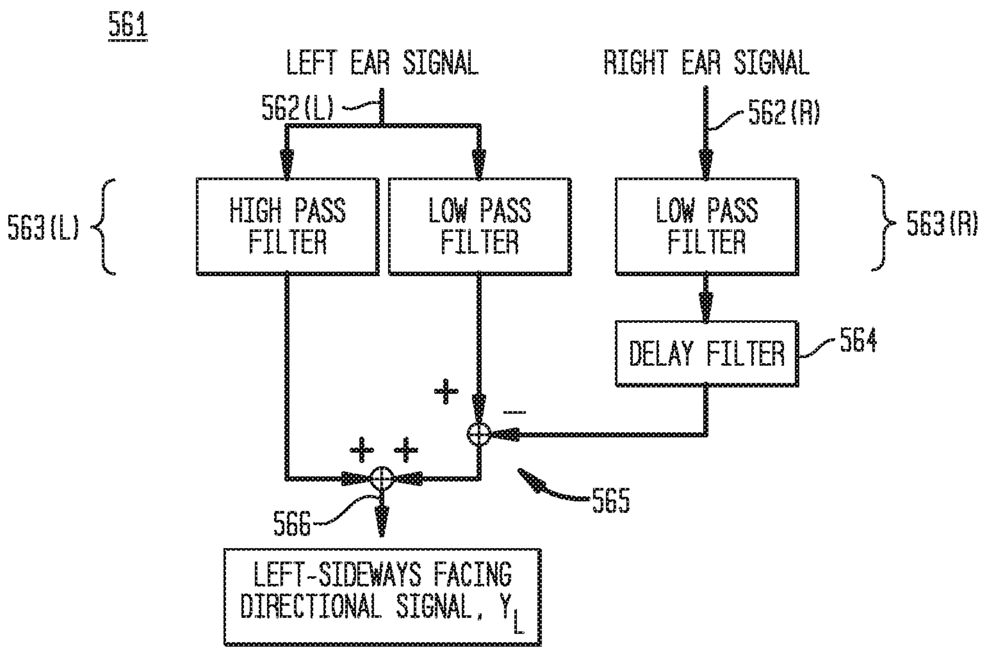
FIG. 5 is a functional block diagram illustrating the basic mechanism of a filter-and-sum beamformer using one or more microphones from a left-side hearing device, and one or more microphones from a right-side hearing device, in accordance with certain embodiments presented herein.

FIG. 5 is a functional block diagram illustrating the basic mechanism of a filter-and-sum beamformer 561 using one or more microphones from a left-side hearing device, and one or more microphones from a right-side hearing device. For ease of description, the example of FIG. 5 will be described with reference to cochlear implant system 100 of FIGS. 1A-1E.

In the example of FIG. 5, the sound signals originate from the right side of the head 101 of the recipient. The cochlear implant 102R receives/captures sound signals with the one or more microphones 118R therein and generates right-side microphone signals 562R representing the sound signals received at the right-side of the head 101. Similarly, cochlear implant 102L receives/captures sound signals with the one or more microphones 118L therein and generates left-side microphone signals 562L representing the sound signals received at the left-side of the head 101. In the example of FIG. 5, the right-side microphone signals 562R are low pass filtered at filter block 563R, while the left-side microphone signals 562L are both high pass filtered and low pass filtered at filter block 563L.

As noted, sound sounds arrive earlier at the microphone(s) positioned closest to the sound source and, as such, in the example of FIG. 5, the sound signals coming from the right will arrive earlier in the right-side microphone(s) 118R than in the left-side microphone(s) 118L. By delaying the signals from the right microphone(s) 118R at delay module 564, the signals 562L and 562R from the left-side and right-side microphones will be aligned in time. As such, the undesired signal portions can be cancelled out by subtracting the delayed version of the right-side microphone signals 562R from the left-side microphone signals 562L at block 565. The result is a left-sideways-facing directional signal 566. In signal 566, sounds that come from directions other than the right side will not be cancelled or will be only partly cancelled.

FIG. 5 illustrates a specific embodiment in which the filter-and-sum is only applied in a specific frequency region, e.g., only the low frequencies where there is no acoustic head shadow. The frequency cut-off is a parameter that can be tuned, but it also to be appreciated that other embodiments are possible (e.g., the filter-and-sum is only applied across all or multiple frequency regions).

In summary, FIG. 5 illustrates sideways directionality (e.g., generation of a left-sideways-facing directional signal) that is obtained with a filter-and-sum beamformer. Again, in FIG. 5, the beamformer 561 is only applied in the lower frequencies. It is to be appreciated that a similar arrangement could be implemented to generate a right-sideways-facing directional signal where the left-side microphone signals 562L are delayed and then subtracted from the right-side microphone signals 562R.

A filter-and-sum beamformer has a typical high-pass characteristic, such that some low frequency boosting could be desirable (not shown in FIG. 5). Another phenomenon that should be considered is spatial aliasing. However, for the higher frequencies where spatial aliasing could be expected, ILDs are present. As such, to attenuate sounds from, for example, −90 degrees, the signals of the left-side and right-side microphones should be aligned in phase and amplitude (taking into account the ILD). As such, spatial aliasing is expected to only play a minor role, such that the beamformer techniques presented herein could be applied both in the low and the high frequencies to maximize head shadow enhancement.

Figure 6:
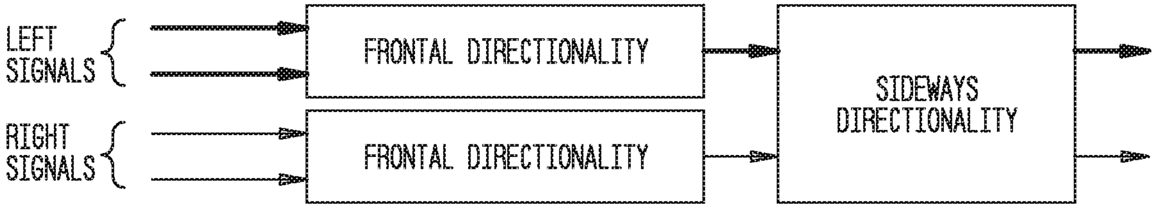
FIG. 6 is a schematic block diagram illustration the use of frontal directionality in combination with sideways directionality, in accordance with certain embodiments presented herein.

As noted above, more microphones in the lateral direction can provide stronger contralateral attenuation. Moreover, more microphones (in any location) provide more freedom to adapt the directionality pattern. For example, two (or three) microphones in the frontal direction per device results in an array of four (or six) microphones. Such an array could be used to achieve frontal directionality in combination with sideways directionality. This is generally shown in FIG. 6. In such examples, a frontal directionality pattern is applied first within each device (e.g., generate a first front-facing directional signal for sound signals captured at the right-side hearing device and generate a second front-facing directionality pattern for sound signals captured at the left-side hearing device), and then the sideways directionality, for example as shown in FIG. 5, is applied to those signals. As a result, only one set of signals would be streamed from each hearing device to the other.

Frontal directionality can be combined with sideways directionality in a number of different manners. For example, each hearing device could first calculate a front directional pattern and then combine across ears (using the interaural magnification) to shift the pattern to each side (e.g., end result is something more pointing to approximately 45 degrees). In another example, the frontal directional pattern could have a zero at 180 degrees, and superposed, a sideways directional pattern with a null at 90 degrees, such that there are two zeros (which is something else than having a null somewhere in between). Moreover, any static beamformer of 2N microphones (N left, N right) is created as a sum of 2N filtered signals (in the simplest version, this "filter" is just a delay and a flip of polarity, to obtain filter-and-sum). To make the data-transfer between devices as efficient as possible, the sum of N filtered signals can be done in the left device, then sent to the right device, then summed with the other N filtered signals of the right device—and vice versa for the left side.

In general, a microphone array consisting of N microphones (e.g., N/2 per hearing device and/or with some external microphones) can be used to design an optimal filter-and-sum beamformer. Each of the N microphone signals is filtered (the delay that is discussed before is only a spatial case of such a filter), and then all filtered signals are summed together. The filters can be tuned to obtain (or approximate) a certain (e.g., frequency-dependent) directional pattern that is desired. Here again, it is advisable to first apply the filter-and-sum within each hearing device (potentially with different filters for the left and right beamformer), and then stream the resulting signal to the other prosthesis to minimize the amount of data that is streamed.

As noted above, the generation of sideways-facing directional signals utilizes the sending or exchange (e.g., streaming) of the received sound signals, processed versions of the sound signals, and/or data associated with the received sound signals between the binaural hearing devices (e.g., via bidirectional wireless link 121 in the example of FIGS. 1A-1E). The sound signals, processed versions of the sound signals, and/or other data associated with the sound signals sent from one of the binaural hearing devices to the contralateral hearing device is sometimes referred to herein as "sound signal data."

In accordance with certain embodiments presented herein, the sound signal data comprises the full/raw sound signals captured by a hearing device (e.g., the left-side prosthesis sends the sound signals received thereby to the right-side prosthesis and the right-side prosthesis sends the sound signals received thereby to the left-side prosthesis). However, in other embodiments, the sound signal data can be compressed (e.g., restricted/reduced) before being sent from one hearing device to the contralateral hearing device.

For example, in some embodiments, application of the frontal directionality within each device can be applied before sending sound signal data to the contralateral hearing device, as discussed above. As noted above, application of the frontal directionality, to generate a front-facing directional signal that is sent from the first to the second hearing device, and vice versa, reduce the amount of data that is sent between the prostheses (e.g., the complete sound signals are not sent, only a specific portion associated with the frontal directionality pattern). In other examples, the sound signal can be compressed by constraining the frequency region in which the sideways directionality is applied, thereby reducing the amount of data that is sent to the contralateral prosthesis as part of the filter-and-sum beamformer. For example, if sideways directionality is only applied below 1500 Hz, a sampling frequency of 3000 Hz is sufficient for the frequency region of interest. In still other examples, the beamformer can be implemented in the frequency domain and only phase information is streamed between the prostheses (e.g., the sound signal data comprises only phase information associated with the sound signals). The phase information of the signal could be sufficient as the amplitude spectrum in the left and right device should be equal (e.g., assuming sound sources in the far-field and omnidirectional microphones), or equalized (e.g., sound sources in the near-field, or when cancelling out natural ILDs). It is to be appreciated that these techniques are merely illustrative and that, in certain embodiments, other types of compression can be applied to reduce the amount of data transferred between the two devices.

In summary, the above description illustrates that, in accordance with embodiments presented herein, sideways-facing directionality patterns are used to generate sideways-facing directional signals from the sound signals received at the left-side and right-side hearing devices of the binaural hearing system. The result is the generation of a first (e.g., left) sideways-facing directional signal and a second (e.g., right) sideways-facing directional signal. As detailed below, in accordance with embodiments presented herein, interaural magnification is applied to the first sideways-facing directional signal and the second sideways-facing directional sound signal in order to magnify the interaural level differences (ILDs) present between the first sideways-facing direction sound signal and the second sideways-facing direction sound signal.

As used herein, interaural magnification refers to a process that magnifies/amplifies binaural cues, including interaural time differences (ITDs) and interaural level differences (ILDs) between two binaural signals, at each instant in time. In the embodiments presented herein, the interaural magnification can be achieved with frame-based processing where the signal from the left-side prosthesis (e.g., the first sideways-facing directional signal) and the signal from the right-side prosthesis (e.g., the second sideways-facing directional signal) are divided into frames (e.g., overlapping and windowed). In each frame, an interaural amplification/magnification transfer function is calculated between the left and right signals, that is, a filter that transforms the left signal into the right signal or vice versa. The filter contains the ITD and ILD and, as such, re-applying the filter on the right signal, the ILD and ITD are doubled. The same can be done for the left signal, resulting in an ILD and ITD amplification of factor 4. The amplification factor can be tuned by more or less (fractional) application of the amplification transfer function, as explained below.

In accordance with the embodiments presented herein, the interaural magnification can be performed at each of the two binaural hearing devices. However, as described below with reference to Equations 1-L/1-R, 2-L/2-R, 3-L/3-R, and 4-L/4-R, the interaural magnification requires making opposing adjustments at each of the two hearing devices. That is, at the left-side hearing device, the interaural magnification is performed to magnify the binaural cues (e.g., ILDs) of the left sideways-facing directional signal relative to the right sideways-facing directional signal (e.g., increase level of sounds in left ear that are higher relative to the right ear and decrease level of sounds in left ear that are lower relative to the right ear). At the right-side hearing device, the interaural magnification is performed to magnify the binaural cues (e.g., ILDs) of the right sideways-facing directional signal relative to the left sideways-facing directional signal (increase level of sounds in right ear that are higher relative to the left ear and decrease level of sounds in right ear that are lower relative to the left ear). These techniques can also be "asymmetric" in the sense that signals will may not be amplified and only attenuated, by setting the maxgain as described below to 0 dB.

The interaural magnification generates a first or left-side magnified binaural signal at the left-side hearing device and second or right-side magnified binaural signal at the right-side hearing device. The signals are "magnified" in that relative ILD cues (e.g., right to left or left to right) are magnified/amplified relative to the cues that would be present (e.g., naturally or after beamforming) between the two sides of the head.

In certain embodiments, the interaural magnification can be performed in the frequency domain via application of short-time Fourier transform to the signals. That is, in each frame, the Fourier transform is applied and the interaural transfer function is calculated as a pointwise division of the two spectra. The application of this transfer function is a pointwise multiplication with the original spectrum. Magnification can be tuned by adding an exponent α to the transfer function. Mathematically, the transfer function for magnification of the first (left) sideways-facing directional signal is represented by Equation 1-L, below.

$$Y_{L,enhanced} = Y_L\left(\frac{Y_L}{Y_R}\right)^{\alpha}, \quad \text{Equation 1-L}$$

where $Y_{L,enhanced}$ is the left-side magnified binaural signal, $Y_L$ is the left sideways-facing directional signal, and $Y_R$ is the right sideways-facing directional signal.

To avoid instabilities in the division, an extra term E can be added, as shown below in Equation 2-L.

$$Y_{L,enhanced} = y_L\left(\frac{Y_L+\varepsilon}{Y_R+\varepsilon}\right)^{\alpha} \quad \text{Equation 2-L}$$

In certain embodiments, the interaural magnification transfer function may be designed so as to only amplify the ILDs. In such embodiments, only the amplitude spectra have to be considered, as shown below in Equation 3-L.

$$Y_{L,enhanced} = y_L\left(\frac{|Y_L|+\varepsilon}{|Y_R|+\varepsilon}\right)^{\alpha} \quad \text{Equation 3-L}$$

In certain embodiments, to avoid extra irregularities, the gains can be constrained to a certain range, as shown below in Equation 4-L.

$$Y_{L,enhanced} = y_L \min\left(\max\left(\left(\frac{|Y_L| + \varepsilon}{|Y_R| + \varepsilon}\right)^{\alpha}, maxgain\right), mingain\right) \quad \text{Equation 4-L}$$

Finally, the gains can be low-pass filtered (e.g., smoothed in time) to avoid sudden gain changes.

As noted, Equations 1-L, 2-L, 3-L, and 4-L all correspond to an interaural transfer function for magnification of the left (first) sideways-facing directional signal relative to the right (second) sideways facing directional signal. Equations 1-R, 2-R, 3-R, and 4-R, below, all each equivalents to Equations 1-L, 2-L, 3-L, and 4-L, respectively, for magnification of the right sideways-facing directional signal relative to the left sideways-facing directional signal.

$$Y_{R,enhanced} = Y_R\left(\frac{Y_R}{Y_L}\right)^{\alpha}, \quad \text{Equation 1-R}$$

where $Y_{R,enhanced}$ is the right-side magnified binaural signal, $Y_R$ is the right sideways-facing directional signal, and $Y_L$ is the left sideways-facing directional signal.

$$Y_{R,enhanced} = Y_R\left(\frac{Y_R + \varepsilon}{Y_L + \varepsilon}\right)^{\alpha} \quad \text{Equation 2-R}$$

$$Y_{R,enhanced} = Y_R\left(\frac{|Y_R| + \varepsilon}{|Y_L| + \varepsilon}\right)^{\alpha} \quad \text{Equation 3-R}$$

$$Y_{R,enhanced} = Y_R \min\left(\max\left(\left(\frac{|Y_R| + \varepsilon}{|Y_L| + \varepsilon}\right)^{\alpha}, maxgain\right), mingain\right) \quad \text{Equation 4-R}$$

FIG. 7 is a schematic diagram generally illustrating the operations of Equations 1-L/1-R, 2-L/2-R, 3-L/3-R, and 4-L/4-R. In the example of FIG. 7, the magnification of the ILDs is applied in the frequency domain, thus $Y_L$, $Y_R$, $Y_{L,\ enhanced}$, and $Y_{R,\ enhanced}$ are short-term spectra.

Similarly to the sideways-facing beamformers described above, interaural magnification does not require explicit calculation of interaural time and level differences or sound locations. However, the interaural magnification relies upon the sending (e.g., streaming) of sound data between the left and right prosthesis. However, similar to the sideways-facing beamformers, the sound data sent from a first hearing device to a second device, or vice versa, for use in performing the interaural magnification can be reduced/compressed.

For example, in certain embodiments, the interaural magnification could only be applied to certain frequency ranges and, as such, only the sound data associated with those frequency ranges would be sent between the binaural prostheses. In other embodiments, if only the ILDs are to be magnified, only the amplitude spectra is sent between the binaural prostheses or, if only the ITDs are to be magnified, only the phase spectra is sent between the binaural prostheses. As an example, an embodiment could include sending phase spectra in low frequencies (where natural ITDs are most important), and amplitude spectra in high frequencies (where natural ILDs are most important).

As detailed above, the use of the static sideways-facing beamformers (sideways-facing directionality patterns) to generate sideways-facing directional signals at two binaural hearing devices increases the ILDs between the two prostheses, particularly at lower frequencies. However, the resulting ILDs obtained by the static sideways-facing beamformer are not always as large as theoretically predicted due to, for example, room reverberation, which deteriorates beamformer behavior and/or other factors. The small size of the ILDs can limit or prevent the use of the ILDs in subsequent sound processing operations. Moreover, apart from the directionality pattern, there is little freedom to tune the ILDs (e.g., increase them even more). However, application of interaural magnification to sideways-facing directional signals overcomes the shortcomings of static sideways-facing beamformers. In particular, if the obtained ILDs (even small ones) are introduced by sideways-facing beamformers in the low frequencies, the ILDs can be further amplified with the interaural magnification (whereas if applied alone, interaural magnification cannot provide low frequency ILDs since, without static sideways-facing beamformers, there are little to no acoustic ILDs in the low frequencies to be enhanced). The use of interaural magnification with the static sideways-facing beamformers also provides more freedom to tune the ILD patterns, in particular by choosing a certain directional pattern (e.g., FIGS. 3A, 3B, etc.), which can be amplified as desired by tuning the magnification exponent α, as detailed above. In addition, the sideways-facing beamformers and the interaural magnification can each be applied in both the lower and/or the higher frequency regions.

Figure 8:
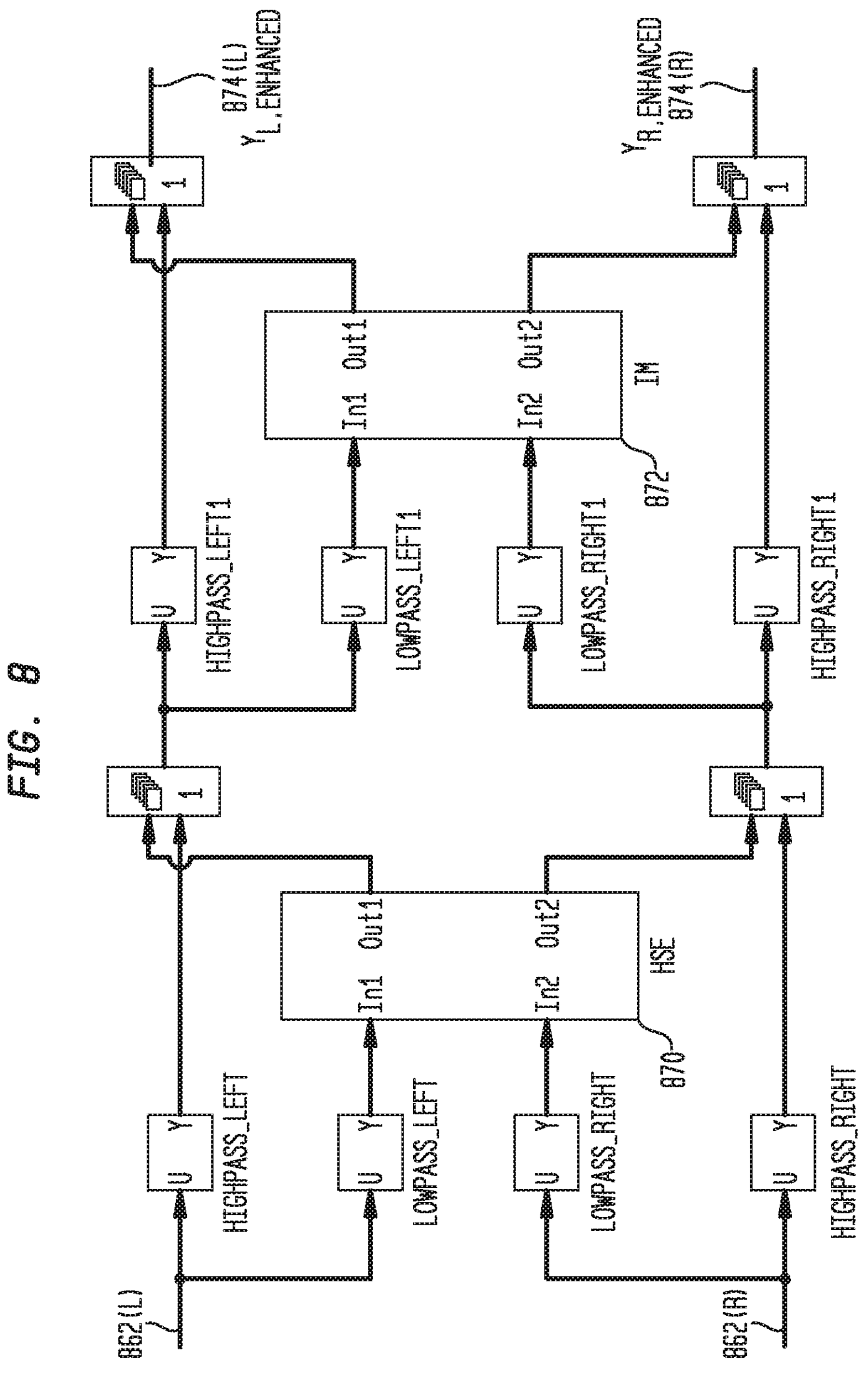
FIG. 8 is a schematic diagram illustrating the use of sideways-facing beamforming with interaural magnification, in accordance with certain embodiments presented herein.
Figures 9A, 9B, 9C, 9D, 9E:
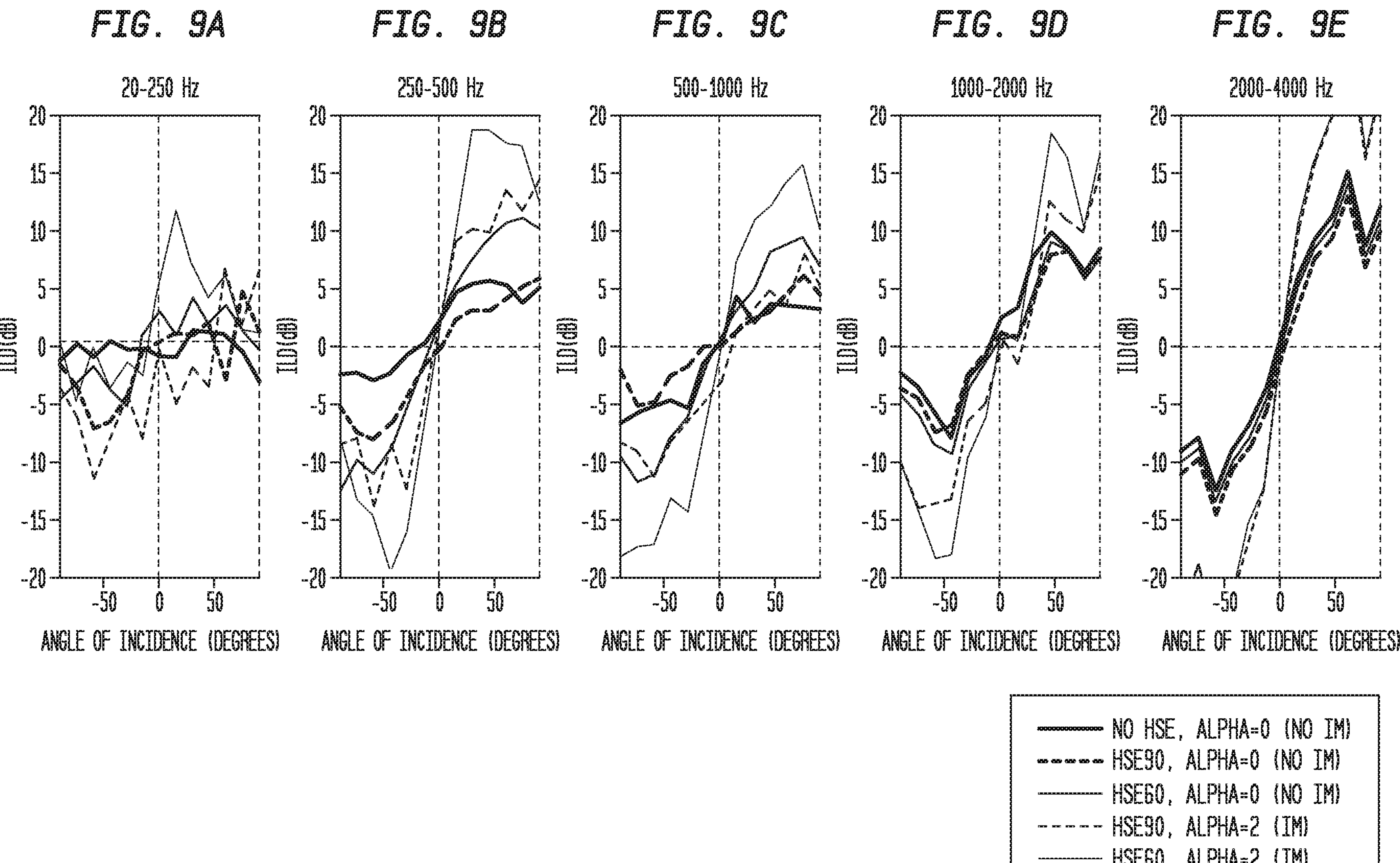
FIGS. 9A, 9B, 9C, 9D, and 9E are graphs illustrating the results of simulations of the use of sideways-facing beamforming with interaural magnification for different parameter settings, in accordance with certain embodiments presented herein.

FIG. 8 is a functional schematic diagram illustrating the use of sideways-facing beamforming with interaural magnification, in accordance with certain embodiments presented herein. More specifically, FIG. 8 illustrates operations of a binaural hearing system comprising a first (left) hearing device and a second (right) hearing device. In generally, the functional blocks shown in FIG. 8 can represent operations performed across one or both the first and the second hearing devices.

In the example of FIG. 8, sound signals 862(L) are received at the first hearing device and sound signals 862(2) are received at the second hearing device. The sound signals 862(L) and 862(R) are used to perform sideways-facing beamforming, as represented by block 870. That is, block 870 represents the sideways-facing beamformers (HSE) that generate the sideways-facing directional signals, $Y_L$ and $Y_R$. In FIG. 8, block 872 represents the interaural magnification (IM) that magnifies the binaural cues present between the sideways-facing directional signals $Y_L$ and $Y_R$. As such, the outputs shown in FIG. 8 comprise the left-side magnified binaural signal 874(L) ($Y_{L,enhanced}$) and the right-side magnified binaural signal 874(R) ($Y_{R,enhanced}$). These magnified binaural signals would then be used for further sound processing at each of the first and second hearing devices, respectively.

The specific arrangement shown in FIG. 8 utilizes two exchanges of data (streaming of sound) from the left to the right prosthesis (and vice versa), namely once for the sideways-facing beamforming, and once for the interaural magnification. In other embodiments, the sound data exchange can only take place once and, a discussed above, the sound data exchange be optimized further by considerate compression of the sound signals.

FIGS. 9A, 9B, 9C, 9D, and 9E illustrate the results of simulations of the use of sideways-facing beamforming with interaural magnification for different parameter settings (e.g., different directional patterns and different values of alpha). In these examples, sideways-facing beamformers are applied only below 2000 Hz, while interaural magnification is applied at all frequencies. It can be seen that the largest ILDs are obtained when the beamformer null is at 60 degrees (e.g., HSE 60), and a magnification exponent alpha of 2 is chosen. These examples present a real-time implementation, with BTE earpieces worn by an artificial manikin placed in a loudspeaker arc with 13 loudspeakers. In these examples, "no HSE" means no sideways-facing beamformer (that is, an omnidirectional microphone), "HSE60" means sideways-facing beamformer with null at 60 degrees, and "HSE90" means sideways-facing beamformer with null at 90 degrees. Alpha is the magnification exponent of the interaural magnification (IM).

The sideways-facing beamformers described above with reference to FIGS. 3A-9E are "static" beamformers, meaning the beamformers have a fixed/static directionality. The use of static beamformers provides stable binaural cues. As noted above, the attenuation of contralateral sounds in each ear (the head shadow effect) is known to be very effective in improving speech understanding in noise, while also providing interaural level differences to localize sound sources. However, the attenuation is not equal for all contralateral angles, such that some noise sources are better attenuated than others, both with natural head shadow, as well as with head shadow enhancement with static sideways-facing beamformers.

The attenuation of contralateral sounds in each ear (the "head shadow") is known to be very effective in improving speech understanding in noise, while also providing interaural level differences to localize sound sources. However, the attenuation is not equal for all contralateral angles, such that some noise sources are better attenuated than others, both with natural head shadow, as well as with head shadow enhancement with static sideways facing beamformers. Moreover, static beamformers often rely on certain microphone characteristics, that is, the beamformer filters are optimized for certain amplitude and phase responses of the microphones. Slight microphone mismatches (e.g., due to production or wear) can deteriorate beamformer performance if the filters are fixed.

Beamformers that steer their directionality patterns adaptively, that is, beamformer filters are adapted in time, to minimize noise power from contralateral side at each instant in time (left device minimizes power from right side, right device minimizes power from left side). Or, in other words, adaptive beamformers that are constrained to not attenuate sound from the ipsilateral (and frontal) side in each device. As such, presented herein are alternative embodiments to optimize the contralateral attenuation of noise sources by using constrained adaptive sideways-facing beamformers (non-fixed/adaptive directionality).

Figure 10:
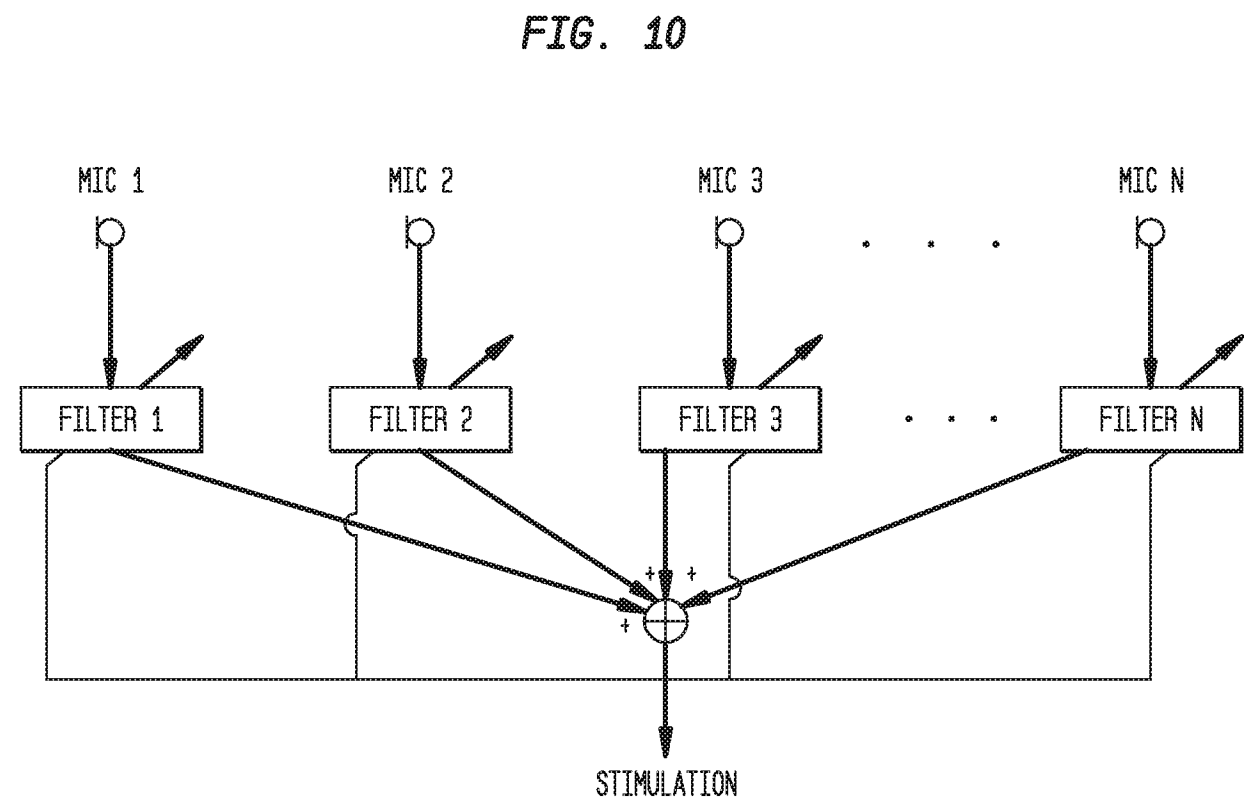

An adaptive beamformer is a (filter-and-sum) beamformer for which the (filter) coefficients are adapted in time, as shown in FIG. 10. The adaptation is performed based on rules that aim to minimize noise at each instant in time while meeting certain constraints. Typically, this constraint is that speech (or, in general, the signal of interest) may not be attenuated. Given this constraint, minimization of noise is actually equivalent to minimization of total output power, as the signal of interest is preserved.

The adaptation time is a design parameter of the beamformer. The constraint to not attenuate signals of interest (e.g., speech) is often translated to a constraint to not attenuate frontal signals. The techniques presented herein propose to adapt/extend the constraint to not attenuate ipsilateral signals at each side of the head.

There are many types of adaptive beamformers that can be implemented in accordance the techniques presented. However, described below are two possible implementations.

One way to achieve adaptive directionality is through the use of an adaptive directional microphone (ADM). More specifically, such adaptive directionality can be achieved by combining two back-to-back cardioids (one facing to the left, and one to the right) with a single parameter $\alpha$ that is tuned to minimize the noise power, as given below in Equations 5-L an 5-R and in FIG. 11. The parameter $\alpha$ is an adaptive parameter that is optimized at each instant in time ("adapted") to minimize total incoming power. The parameter is constrained such that no frontal or ipsilateral signals are attenuated.

$$y_{left}(t)=\text{"left cardioid"}+\alpha\times\text{"right cardioid"}, \quad \text{Equation 5-L}$$

where $y_{left}(t)$ is the resulting adaptive directional sound signal at the left hearing device of a binaural system.

$$y_{right}(t)=\text{"right cardioid"}+\alpha\times\text{"left cardioid"} \quad \text{Equation 5-R}$$

where $y_{right}(t)$ is the adaptive directional sound signal at the left hearing device of a binaural system.

In the above examples, if $\alpha$ is constrained between 0 and 1, then the beamformer null will be steered between 90 degrees for $\alpha$=0 and 180 degrees for $\alpha$=1. Frontal attenuation can be avoided by constraining $\alpha$ between 0 and a constant that is smaller than 1. The adaptive directionality can also be implemented in frequency-dependent way, such that $\alpha$ is an adaptive filter.

In certain embodiments, the adaptive directional microphone (ADM) may comprise four (4) directional microphones (one left-facing, one right-racing, then also one front-facing and one backward-facing) to minimize both rear and contralateral noise. Alternatively, it may be possible to first apply the adaptive directional microphone techniques in the front-back direction, then he apply adaptive directional microphone techniques in the left-right direction. In further embodiments, some additional parametric freedom may be provided in generation of the directional signals.

Figure 12:
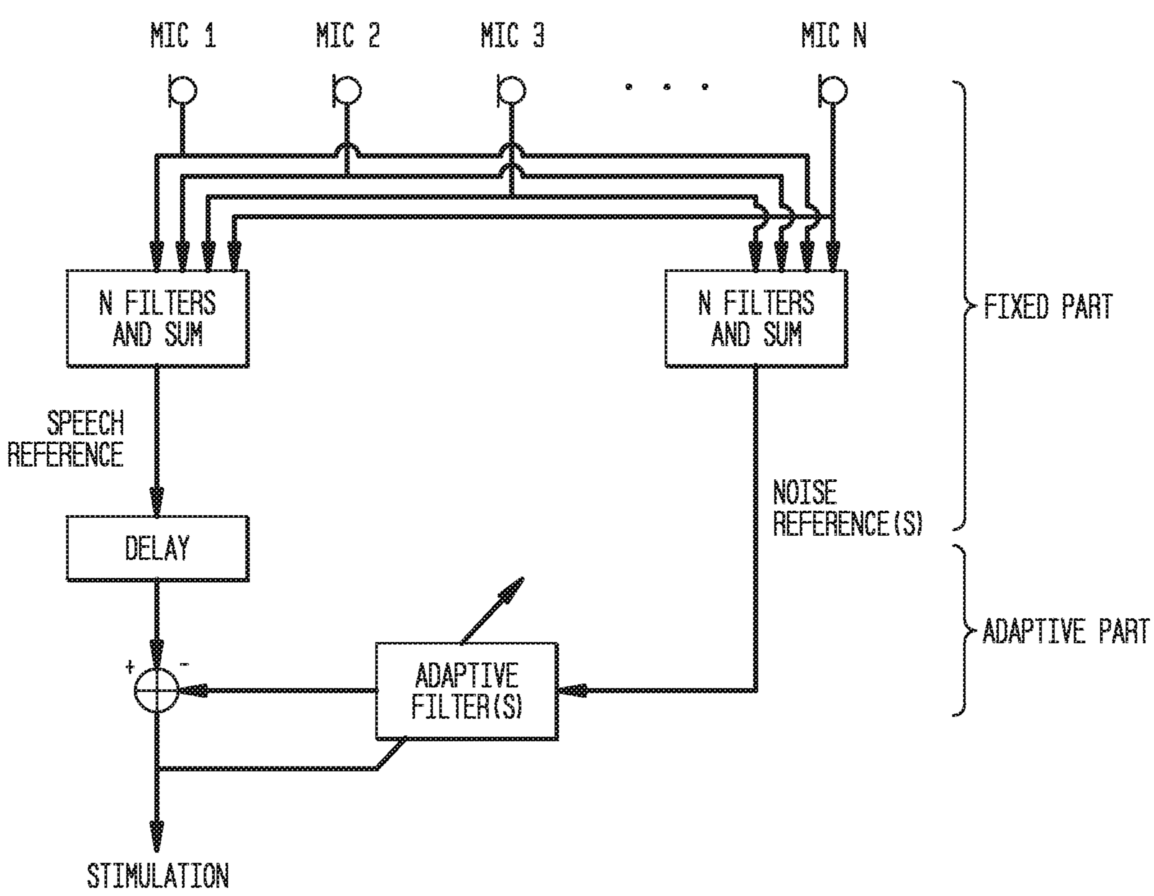

Another way to achieve adaptive directionality, is to use a modified sidelobe canceller (GSC). In particular, a standard sidelobe canceller (GSC) generally uses a speech reference signal (with a static filter-and-sum beamformer) and a noise reference signal(s) (with static beamformer(s) that have their nulls at the angle of the signal of interest). In a second step, the noise that is still present in the speech reference is removed with one or more adaptive filter(s) (in a least-mean-squares manner). This process is generally shown in FIG. 12.

By choosing the speech and noise references, it is possible to obtain in each device an adaptive pattern that attenuates sounds from the contralateral side, or, an adaptive pattern that is constrained so as to not attenuate sounds from the ipsilateral side.

For example, in one embodiment presented herein, signals captured with a frontal facing cardioid are used as the speech reference and signals captured with a sideways-facing cardioid are used as the noise reference. In another embodiment presented herein, signals captured with a sideways-facing cardioid are used as the speech reference and signals captured with a backwards facing cardioid as noise reference. In a further embodiment presented herein, signals captured with a first sideways-facing cardioid are used as the speech reference, and signals captured with a second sideways-facing cardioid having an opposing directionality to the first sideways-facing cardioid, are used as the noise reference. In general, any other combination of static directional patterns (e.g., more complex patterns different form a cardioid) that introduces some asymmetry in the eventual adaptive beamformer could be used in a modified sidelobe canceller presented herein. As with static beamformers, the more microphones in the array, the more advanced the patterns can be designed.

As with static beamformers, the more microphones in the array, the more advanced the patterns can be designed. In some implementations, the filters are only adapted when a voice activity detector (VAD) makes sure that there is no speech present. This is to avoid that the beamformer removes signals of interest, as the signal of interest can also leak in the noise references, for example due to reverberation.

As detailed above, static sideways-facing beamformers with interaural magnification can improve sound localization (based on ILDs) as well as speech understanding in noise (based on SNR improvements). The sideways-facing beamformers with interaural magnification results in ILDs that are static (unless the parameters are adapted), yielding large and robust localization cues. Adaptive sideways-facing beamformers exploit the complementarity of the two ears, but result in ILD-versus-angle functions that are adaptive as well, which might affect localization performance negatively. However, the ILDs will always point in the target/desired direction. This solution is expected to have a beneficial effect on speech understanding, while maintaining strong spatial awareness, as each ear clearly focuses on its own side, while attenuating contralateral sounds as effective as possible.

The sideways-facing beamforming with interaural magnification, as well as adaptive sideways-facing beamforming, can referred to as different types of "microphone directionality" of a hearing device. That is, the sideways-facing beamforming with interaural magnification and/or the adaptive sideways-facing beamforming each generate directional microphone signals that are useable for subsequent sound processing operations. In certain embodiments presented herein, the binaural hearing devices in a binaural hearing system are each configured to automatically select between the sideways-facing beamforming with interaural magnification, the adaptive sideways-facing beamforming, and/or another type of microphone directionality setting. That is, a type of microphone directionality is automatically selected in both the left-side and the right-side prostheses based on an estimated need of the recipient in a given sound environment or listening situation. In addition, beamforming applied within a setting could be adapted based on the sound environment or listening situation (e.g., stronger interaural magnification (alpha) if there is more reverberation).

As such, in accordance with certain embodiments presented, an automated microphone directionality selection process/technique (e.g., algorithm) is used to automatically (i.e., without user intervention) select between the sideways-facing beamforming with interaural magnification, the adaptive sideways-facing beamforming, and/or others type of microphone directionality. The microphone directionality selection techniques process is configured to first extract acoustic features from the received sound signals. The microphone directionality selection process includes the use of a classifier (e.g., neural network) that is configured to use the extracted acoustic features to classify the current sound environment/listening situation of the recipient into one of a number of predetermined "directionality categories." In general, each directionality category corresponds to a set of acoustic features that would make use of a particular type of microphone directionality more advantageous than the other available types of microphone directionality. Each predetermined directionality category is also associated with one type of microphone directionality. As such, when the recipient's current listening situation is categorized as one of the directionality categories, the hearing device selects, and then uses, the type of microphone directionality associated with the selected directionality category.

FIG. 13 is a table 1375 illustrating example directionality categories and the microphone directionality that would be selected in the given directionality category, in accordance with examples presented herein. Table 1375 also illustrates the SNR/ICR that would be present in each of the directionality categories and the general need of the recipient in each of the directionality categories.

In general, the static sideways beamforming with interaural magnification may be most beneficial for sound localization and when there is low noise competing with a target sound. As such, in certain embodiments, a default interaural magnification microphone directionality mode (e.g., static sideways beamforming with interaural magnification) is used to pre-process the sound signals. This default interaural magnification microphone directionality mode, which generates a magnified binaural signal from the sound signals, can be overridden by other microphone directionality based on the sound environment.

In contrast, the adaptive sideways beamformer sacrifices some sound localization performance to better cancel out contralateral sounds, and thus would be preferred when there are multiple sound sources, at least one to the right and a second to the left, especially when the signal-to-noise ratio (SNR) or ipsilateral-to-contralateral ratio (ICR) is lower than a selected threshold.

It is to be appreciated that the information shown in FIG. 13 is merely illustrative and that other directionality categories, other microphone directionality and/or different combinations thereof may be used in alternative embodiments. It is also to be appreciated that other features could be used in automating the selection of microphone directionality, including speech detectors facing forward, to the ipsilateral side, and/or to the rear.

In one example method corresponding to the embodiments of FIG. 13, sound signals are received at a binaural hearing system comprising first and second hearing devices positioned at first and second sides, respectively, of a head of a recipient. The first hearing device executes a default interaural magnification microphone directionality mode (e.g., static sideways beamforming with interaural magnification) to pre-process the sound signals, where the default interaural magnification microphone directionality mode generates a magnified binaural signal from the sound signals. A sound environment of the first hearing device is classified based on the sound signals and a second microphone directionality mode for pre-processing the sound signals is determined based on the classifying of the sound environment. The default interaural magnification microphone directionality mode is then overridden with the second microphone directionality mode to generate a second directional signal. Sound processing is then performed based on the second directional signal.

Figure 14:
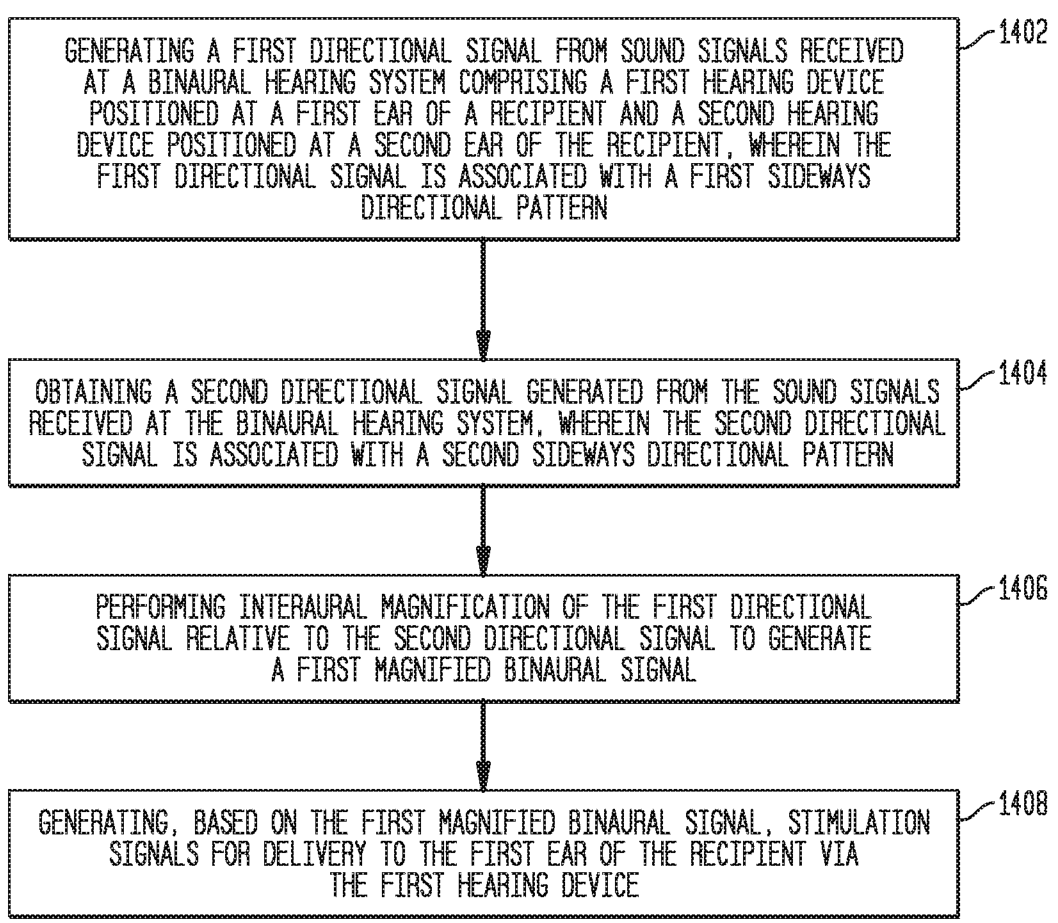
FIG. 14 is a flowchart illustrating an example method, in accordance with certain embodiments presented herein.

FIG. 14 is a flowchart of a method 1400, in accordance with embodiments presented herein. Method 1400 begins at 1402 where a first hearing device of a binaural hearing system generates a first directional signal from sound signals received at the binaural hearing system. The first directional signal is associated with a first sideways directional pattern and the first hearing device is positioned at a first ear of a recipient. The binaural hearing system also comprises a second hearing device positioned at a second ear of the recipient. At 1404, the first hearing device obtains a second directional signal generated from the sound signals received at the binaural hearing system, wherein the second directional signal is associated with a second sideways directional pattern that is a mirror image of the first sideways directional pattern. In certain arrangements, the raw (non-enhanced, potentially with frontal directionality and/or compressed) signals are sent from the right ear to the left ear, and vice versa, and then used to calculate the ipsilateral pattern and contralateral pattern within the same device (this means that these calculations are done twice, once in each device).

At 1406, the first hearing device performs interaural magnification of the first directional signal relative to the second directional signal to generate a first magnified binaural signal. At 1408, the first hearing device generates, based on the first magnified binaural signal, stimulation signals for delivery to the first ear of the recipient via the first hearing device.

Figure 15:
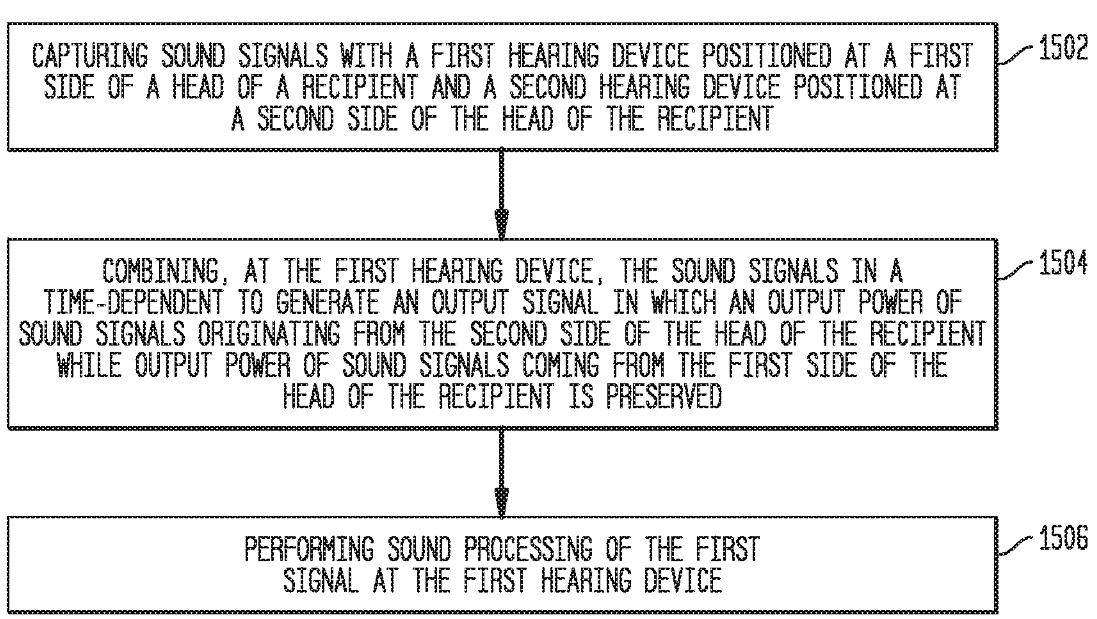
FIG. 15 is a flowchart illustrating another example method, in accordance with certain embodiments presented herein.

FIG. 15 is a flowchart of another method 1500, in accordance with embodiments presented herein. Method 1500 begins at 1502 where sound signals are captured with a first hearing device positioned at a first side of a head of a recipient and a second hearing device positioned at a second side of the head of the recipient. At 1504, the sound signals are combined, at the first hearing device, in a time-dependent manner to generate an output signal in which an output power of sound signals originating from the second side of the head of the recipient is minimized while output power of sound signals coming from the first side of the head of the recipient is preserved. At 1506, sound processing is performed based on the first signal at the first hearing device.

FIG. 16 is functional block diagram illustrating details of a binaural hearing system 1600, in accordance with certain embodiments presented herein. As shown, the binaural hearing system 1600 comprises a first hearing device 1602L and a second hearing device 1602R positioned at opposing ears of a recipient.

As shown, the first hearing device 1602L comprises a plurality of microphones 1618L, a bidirectional wireless transceiver 1620L, a forward directional microphone processing block 1680L, a sideways directional microphone processing block 1682L, a sound analysis and control block 1684L, an interaural magnification block 1686L, a selector/mixing block 1688L, and a stimulation processing and output block 1690L. Similarly, the second hearing device 1602R comprises a plurality of microphones 1618R, a bidirectional wireless transceiver 1620R, a forward directional microphone processing block 1680R, a sideways directional microphone processing block 1682R, a sound analysis and control block 1684R, an interaural magnification block 1686R, a selector/mixing block 1688R, and a stimulation processing and output block 1690R.

In operation, the microphones 1618L/1618R capture sounds at the left and right hearing devices 1602L/1602R, respectively, while the wireless transceivers 1620L/1620R facilitate the bidirectional exchange of information/data between the hearing devices. The optional forward directional microphone processing blocks 1680L/1680R are configured to generate frontal directional signals, as described above, for example, with reference to FIG. 6. Similarly, the sideways directional microphone processing blocks 1682L/1682R are configured to perform sideways beamforming (e.g., generate sideways facing directional signals) as described above, for example, with reference to FIGS. 3A, 3B, 4, 5, 7, etc. The interaural magnification blocks 1686L/1686R are configured to perform interaural magnification as described above, for example, with reference to FIGS. 7, 8, 9A-9E, etc.

In addition, the sound analysis and control blocks 1684L/1684R are configured to perform the environmental classification and the automated microphone directionality selection techniques described above with reference to FIG. 10. The selector/mixing blocks 1688L/1688R operate under the control of other blocks to control the final output signals that are provided to the stimulation processing and output blocks 1690L/1690R.

As noted, it is to be appreciated that FIG. 16 illustrates an example binaural hearing system that integrates a number of different embodiments described elsewhere herein. Accordingly, it is to be appreciated that a number of the functional blocks shown in FIG. 16 may be omitted in various embodiments. For example, certain embodiments may omit the forward directional microphone processing blocks 1680L/1680R, omit the sound analysis and control blocks 1684L/1684R, etc.

Merely for ease of description, the techniques presented herein have primarily described herein with reference to an illustrative medical device system, namely a bilateral cochlear implant system that delivers electrical stimulation to both ears of a recipient. However, it is to be appreciated that the techniques presented herein may also be used with a variety of other medical devices that, while providing a wide range of therapeutic benefits to recipients, patients, or other users, may benefit from the techniques presented. For example, a bilateral cochlear implant system in accordance with embodiments presented herein may also deliver acoustic stimulation to one or both ears of the recipient (e.g., one or more of the cochlear implants is an electro-acoustic cochlear implant). It is also to be appreciated that the two cochlear implants of a bilateral cochlear implant system in accordance with embodiments presented need not be identical with respect to, for example, the number of electrodes used to electrically stimulate the cochlea, the type of stimulation delivered, etc. Furthermore, it is to be appreciated that the techniques presented herein may be used with other binaural hearing systems, such as systems including acoustic hearing aids, bone conduction devices, middle ear auditory prostheses, direct acoustic stimulators, other electrically simulating auditory prostheses (e.g., auditory brain stimulators), stand-alone microphones, etc. The techniques presented herein may also be used with vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation, etc.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:

generating a first sideways-facing directional signal from sound signals received at a binaural hearing system comprising a first hearing device positioned at a first ear of a recipient and a second hearing device positioned at a second ear of the recipient, wherein the first sideways-facing directional signal is associated with a first sideways directional pattern;

obtaining a second sideways-facing directional signal generated from the sound signals received at the binaural hearing system, wherein the second sideways-facing directional signal is associated with a second sideways directional pattern;

performing interaural magnification of the first sideways-facing directional signal relative to the second sideways-facing directional signal to generate a first magnified binaural signal that magnifies interaural level differences (ILDs) present in the first sideways-facing directional signal relative to ILDs present in the second sideways-facing directional signal; and using the first magnified binaural signal to generate stimulation signals for delivery to the first ear of the recipient via the first hearing device.

2. The method of claim 1, further comprising:

performing interaural magnification of the second sideways-facing directional signal relative to the first sideways-facing directional signal to generate a second magnified binaural signal, wherein the interaural magnification of the second sideways-facing directional signal relative to the first sideways-facing directional signal is generally opposite to the interaural magnification of the first sideways-facing directional signal relative to the second sideways-facing directional signal; and generating, using the second magnified binaural signal, stimulation signals for delivery to a second ear of the recipient via the second hearing device.

3. The method of claim 1, wherein the first sideways directional pattern and the second sideways directional pattern are sideways-facing cardioid patterns each facing laterally from a head of the recipient.

4. The method of claim 1, wherein the first sideways directional pattern and the second sideways directional pattern are each sideways-facing supercardioid polar patterns facing laterally from a head of the recipient.

5. The method of claim 1, wherein the first sideways directional pattern and the second sideways directional pattern are each frequency-dependent polar patterns.

6. The method of claim 1, wherein generating the first sideways-facing directional signal from the sound signals received at the binaural hearing system comprises:

implementing a filter-and-sum beamformer.

7. The method of claim 6, wherein the implementing a filter-and-sum beamformer comprises:

receiving, at the first hearing device, sound data from the second hearing device, wherein the sound data includes sound signals captured by one or more microphones of the second hearing device;

delaying the sound signals received at the second hearing device to generate delayed sound signals; and subtracting the delayed sound signals from sound signals received at one or more microphones of the first hearing device.

8. The method of claim 7, wherein prior to delaying the sound signals, the method comprises:

at least one of band-pass filtering or low-pass filtering the sound signals received at the second hearing device.

9. The method of claim 8, further comprising:

performing low-pass filtering at the second hearing device to generate low-frequency portion of sound signals, wherein the sound data includes only the low-frequency portion of sound signals.

10. The method of claim 1, wherein generating the first sideways-facing directional signal from the sound signals received at the binaural hearing system comprises:

capturing a first set of sound signals with one or more microphones of the first hearing device;

receiving, from the second hearing device, sound data representing a second set of sound signals captured by one or more microphones of the second hearing device; and generating the first sideways-facing directional signal based on the first set of sound signals and the sound data.

11. The method of claim 10, wherein the sound data comprises only a low frequency portion of the second set of sound signals captured by the one or more microphones of the second hearing device.

12. The method of claim 10, wherein the sound data comprises a front-facing directional signal generated from the second set of sound signals captured by the one or more microphones of the second hearing device.

13. The method of claim 10, wherein the sound data comprises only phase information associated with the second set of sound signals captured by the one or more microphones of the second hearing device.

14. The method of claim 1, wherein performing interaural magnification of the first sideways-facing directional signal relative to the second sideways-facing directional signal to generate a first magnified binaural signal comprises:

dividing each of the first sideways-facing directional signal and the second sideways-facing directional signal into time frames; and within each time frame, calculate an interaural magnification transfer function between the first sideways-facing directional signal and the second sideways-facing directional signal, wherein the interaural magnification transfer function amplifies one or more of interaural time differences (ITDs) or interaural level differences (ILDs) present between the first sideways-facing directional signal and the second sideways-facing directional signal within each time frame.

15. The method of claim 14, further comprising:

setting a variable of the interaural magnification transfer function to tune the amplification of the one or more of the ITDs or ILDs present between the first sideways-facing directional signal and the second sideways-facing directional signal within each time frame.

16. The method of claim 14, further comprising:

in each time frame, performing a Fourier transform to each of the first sideways-facing directional signal and the second sideways-facing directional signal; and calculating a pointwise division of a spectrum of the first sideways-facing directional signal with a spectrum of the second sideways-facing directional signal.

17. One or more non-transitory computer readable storage media comprising instructions that, when executed by a processor, cause the processor to:

generate a first sideways-facing directional signal from sound signals received at a binaural hearing system of a recipient, wherein the first sideways-facing directional signal is associated with a first sideways directional pattern;

obtain a second sideways-facing directional signal generated from the sound signals received at the binaural hearing system, wherein the second sideways-facing directional signal is associated with a second sideways directional pattern;

perform interaural magnification of the first sideways-facing directional signal relative to the second sideways-facing directional signal to generate a magnified binaural signal that magnifies interaural level differences (ILDs) present in the first sideways-facing directional signal relative to ILDs present in the second sideways-facing directional signal; and perform sound processing based on the magnified binaural signal to generate, using the magnified binaural signal, stimulation signals for delivery to a first ear of the recipient.

18. The one or more non-transitory computer readable storage media of claim 17, wherein the first sideways directional pattern and the second sideways directional pattern are sideways-facing cardioid patterns each facing laterally from a head of the recipient.

19. The one or more non-transitory computer readable storage media of claim 17, wherein the first sideways directional pattern and the second sideways directional pattern are each sideways-facing supercardioid polar patterns facing laterally from a head of the recipient.

20. The one or more non-transitory computer readable storage media of claim 17, wherein the first sideways directional pattern and the second sideways directional pattern are each frequency-dependent polar patterns.

21. The one or more non-transitory computer readable storage media of claim 17, wherein the instructions operable to generate the first sideways-facing directional signal from the sound signals received at the binaural hearing system comprise instructions operable to:

implement a filter-and-sum beamformer.

22. The one or more non-transitory computer readable storage media of claim 21, wherein the instructions operable to implement a filter-and-sum beamformer comprise instructions operable to:

receive, at a first hearing device, sound data from a second hearing device, wherein the sound data includes sound signals captured by one or more microphones of the second hearing device;

delay the sound signals received at the second hearing device to generate delayed sound signals; and subtract the delayed sound signals from sound signals received at one or more microphones of the first hearing device.

23. The one or more non-transitory computer readable storage media of claim 22, further comprising instructions that, prior to delaying the sound signals, are operable to:

perform at least one of band-pass filtering or low-pass filtering of the sound signals received at the second hearing device.

24. The one or more non-transitory computer readable storage media of claim 23, further comprising instructions operable to:

perform the low-pass filtering at the second hearing device to generate low-frequency portion of sound signals, wherein the sound data includes only the low-frequency portion of sound signals.

25. The one or more non-transitory computer readable storage media of claim 17, wherein generating the first sideways-facing directional signal from the sound signals received at the binaural hearing system comprise instructions operable to:

capture a first set of sound signals with one or more microphones of a first hearing device;

receive, from a second hearing device, sound data representing a second set of sound signals captured by one or more microphones of the second hearing device; and generate the first sideways-facing directional signal based on the first set of sound signals and the sound data.

26. The one or more non-transitory computer readable storage media of claim 25, wherein the sound data comprises only a low frequency portion of the second set of sound signals captured by the one or more microphones of the second hearing device.

27. The one or more non-transitory computer readable storage media of claim 25, wherein the sound data comprises a front-facing directional signal generated from the second set of sound signals captured by the one or more microphones of the second hearing device.

28. The one or more non-transitory computer readable storage media of claim 25, wherein the sound data comprises only phase information associated with the second set of sound signals captured by the one or more microphones of the second hearing device.

29. The one or more non-transitory computer readable storage media of claim 17, wherein the instructions operable to perform interaural magnification of the first sideways-facing directional signal relative to the second sideways-facing directional signal to generate a magnified binaural signal comprise instructions operable to:

divide each of the first sideways-facing directional signal and the second sideways-facing directional signal into time frames; and within each time frame, calculate an interaural magnification transfer function between the first sideways-facing directional signal and the second sideways-facing directional signal, wherein the interaural magnification transfer function amplifies one or more of interaural time differences (ITDs) or interaural level differences (ILDs) present between the first sideways-facing directional signal and the second sideways-facing directional signal within each time frame.

30. The one or more non-transitory computer readable storage media of claim 29, further comprising instructions operable to:

set a variable of the interaural magnification transfer function to tune amplification of the one or more of the ITDs or ILDs present between the first sideways-facing directional signal and the second sideways-facing directional signal within each time frame.

* * * * *